US012754317B2

(12) United States Patent
Josset et al.

(10) Patent No.: US 12,754,317 B2
(45) Date of Patent: Oct. 6, 2026

(54) BUBBLE DETECTION AND CHARACTERIZATION VIA LIDAR

(71) Applicant: The Government of the United States of America, as represented by the Secretary of the Navy, Arlington, VA (US)

(72) Inventors: Damien Josset, Covington, LA (US); David Wang, Slidell, LA (US); Brian Concannon, Lusby, MD (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 458 days.

(21) Appl. No.: 18/476,959

(22) Filed: Sep. 28, 2023

(65) Prior Publication Data

US 2025/0110239 A1 Apr. 3, 2025

(51) Int. Cl.

*G01S 17/88* (2006.01)
*G01N 33/18* (2006.01)
*G01S 7/497* (2006.01)
*G01S 7/499* (2006.01)

(52) U.S. Cl.

CPC .............. *G01S 17/88* (2013.01); *G01N 33/18* (2013.01); *G01S 7/497* (2013.01); *G01S 7/499* (2013.01)

(58) Field of Classification Search

None

See application file for complete search history.

(56) References Cited

U.S. PATENT DOCUMENTS

2021/0041542 A1* 2/2021 Shepard ................ G01S 17/931
2021/0116566 A1* 4/2021 Blum ................ G01N 33/1833

OTHER PUBLICATIONS

Churnside "LIDAR signature from bubbles in the sea", Optics Express vol. 18, No. 8, (Apr. 12, 2010), pp. 8294-8299 (Year: 2010).*

* cited by examiner

*Primary Examiner* — Eric L Bolda
(74) *Attorney, Agent, or Firm* — US Naval Research Laboratory; Nigel R. Fontenot

(57) ABSTRACT

A method includes receiving lidar data associated with remote sensing of moving water, and calibrating the lidar data, the calibration being based on one or more measurements contemporaneously measured with remote sensing of the moving water. The method includes refining the calibrated lidar data, the refinement being based on bubble detection associated with the moving water, where the refining includes discriminating between one or more signals associated with the bubble detection and one or more signals associated with non-bubble background detection. The method includes determining, from the refined lidar data, a bubble mask via feature detection based on depolarization ratio, and determining, based on the bubble mask, one or more bubble characteristics associated with the moving water.

23 Claims, 17 Drawing Sheets

Fig. 1. Top left and bottom: the NRL Shipboard Lidar mounted on the bow of the R/V Sikuliaq vessel. The dark arrows show the position of the lidar acquisition device (small white dot on the bow). Top right: One of the waves that reached the bow.

Fig. 2. Optical transmission path of the NRL shipboard lidar.

Fig. 3. Top: track of the R/V Sikuliaq across the Gulf of Alaska. Bottom left: pressure levels (m/s) during the travel. Bottom right: same as left but for wind speed (m/s).

Fig. 4. Roll of the ship for the lidar data under analyses.

Fig. 7. Depolarization element of the Mueller matrix for spherical particles near the backscatter direction. Using the distributions proposed by Kokhanovsky 2003 (15 μm solid line, 30 μm dashed line).

Fig. 8. Average backscatter coefficient of bubbles and bubbleless lidar profiles.

Fig. 9A. Depolarization of the lidar signal for one extreme case of bubble depth. Green features are bubbles and blue features the ocean (bubbleless) water.

Fig. 9B. Statistic of bubble depth from the bubble mask (e.g., features going from the surface to some depth) as a function of wind speed. The dot is the depth of the bubble cloud shown in Fig. 9A.

Fig. 10. Depolarization of the subsurface signal (higher for extended bubble clouds) as a function of the depolarization of the surface signal (higher for whitecaps).

Fig.11. Left (a): lidar attenuated backscatter intensity (decimal logarithm) for a file starting at 23:08:43Z the 12th December 2019, Middle (b): same as a) but for the lidar depolarization, Right (c) : same as b) but the non-underwater bubble features have been removed with the bubble mask (above water features are filtered at a later step).

Fig. 12. Left: NRL Shipboard Lidar depolarization as a function of wind speed. Right: CALIPSO lidar depolarization as a function of (AMSR-E) wind speed.

Fig. 13. Gradient of the surface intensity (co-polarization channel) as a function of the gradient of the surface depolarization.

Fig. 14. Left: decimal logarithm of the signal below the bubbles cloud.
Right: Two way transmission of the bubble cloud.

Fig. 15. Example of void fraction retrieval for a lidar case in Dec 11, 2019 (21:13:00Z).

BUBBLE DETECTION AND CHARACTERIZATION VIA LIDAR

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, DC 20375, USA; +1.202.767.7230; techtran@nrl.navy.mil, referencing Navy Case #210879.

TECHNICAL FIELD

The present disclosure is related to remote sensing, and more specifically to, but not limited to, detecting and/or deriving properties (e.g., characteristics) of underwater bubble clouds via lidar (e.g., shipboard lidar or the like).

BACKGROUND

All references cited herein are hereby incorporated by reference into the present application in their entirety.

Bubbles are a fleeting, yet omnipresent feature of the ocean. The majority are generated by the breaking of ocean waves, and they are a critical component of the air-sea interface, particularly in high-wind conditions (Woolf et al., 2007). Bubbles play an important role in the biogeochemical cycle through their role in air-sea gas exchange and marine aerosol creation. The presence of bubbles has a considerable influence on ocean optical properties through their strong scattering effect (Davis 1955, Seitz 2011, Czerski 2017, Selmke 2020). Bubbles are of specific interest to the Navy because they can affect the propagation of acoustic signals (Fabre et al. 2009).

Lidar (Light Detection and Ranging) return is sensitive to whitecaps and bubbles (Menzies et al. 1998, Flamant et al. 2003). There is however a very limited number of published studies discussing the lidar return of bubbles in the ocean. The impact of whitecaps on the CALIPSO space lidar return is briefly shown and discussed in (Hu et al. 2008) and (Josset et al. 2010a). In the context of the fundamental lidar equation (Josset et al. 2010b), Josset stresses the importance of performing more studies using lidar depolarization "at high wind speeds when bubbles are forming inside the water column." More recently, (Churnside 2014) has shown and discussed the lidar return of bubbles created by ship wakes.

There are two standard ways to obtain information on the bubble environment: Surface whitecaps coverage fraction from passive instruments, and bubble profiles measured from acoustic backscatter instruments. Traditionally, passive instruments can be mounted on a variety of platforms (ship, aircraft, satellite) and provide full spatial coverage. However the data retrieved from this method is limited to the surface of the water. In some cases, a camera on a truss structure has been used.

Traditional acoustic sensors must be underwater. They are either fixed or slow moving which limits the spatial coverage. They are most sensitive to the presence of a specific bubble size (resonance frequency).

The fact that a lidar signal qualitatively changes in presence of underwater bubbles has been documented on the few publications mentioned herein, but the inventors believe that no one has determined bubble properties or characteristics from lidar data. That is, because of the difficulty of measuring bubbles via lidar (i.e., use the lidar in storm conditions), the inventors believe that there have been no practical methods to extract bubble properties from lidar data.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

Disclosed aspects provide methods and systems for detecting and/or deriving properties (e.g., characteristics) of underwater bubble clouds via lidar (e.g., shipboard lidar or the like).

The present disclosure provides for a method that may include receiving, by a computing device, lidar data, the lidar data being associated with remote sensing of moving water. The method may include calibrating, by the computing device, the lidar data, the calibration being based on one or more measurements contemporaneously measured with remote sensing of the moving water, and refining, by the computing device, the calibrated lidar data, the refinement being based on bubble detection associated with the moving water, wherein the refining comprises discriminating between one or more signals associated with the bubble detection and one or more signals associated with non-bubble background detection. The method may include determining, from the refined lidar data and by the computing device, a bubble mask via feature detection based on depolarization ratio, and determining, based on the bubble mask and by the computing device, one or more bubble characteristics associated with the moving water.

DETAILED DESCRIPTION

Figure 1:
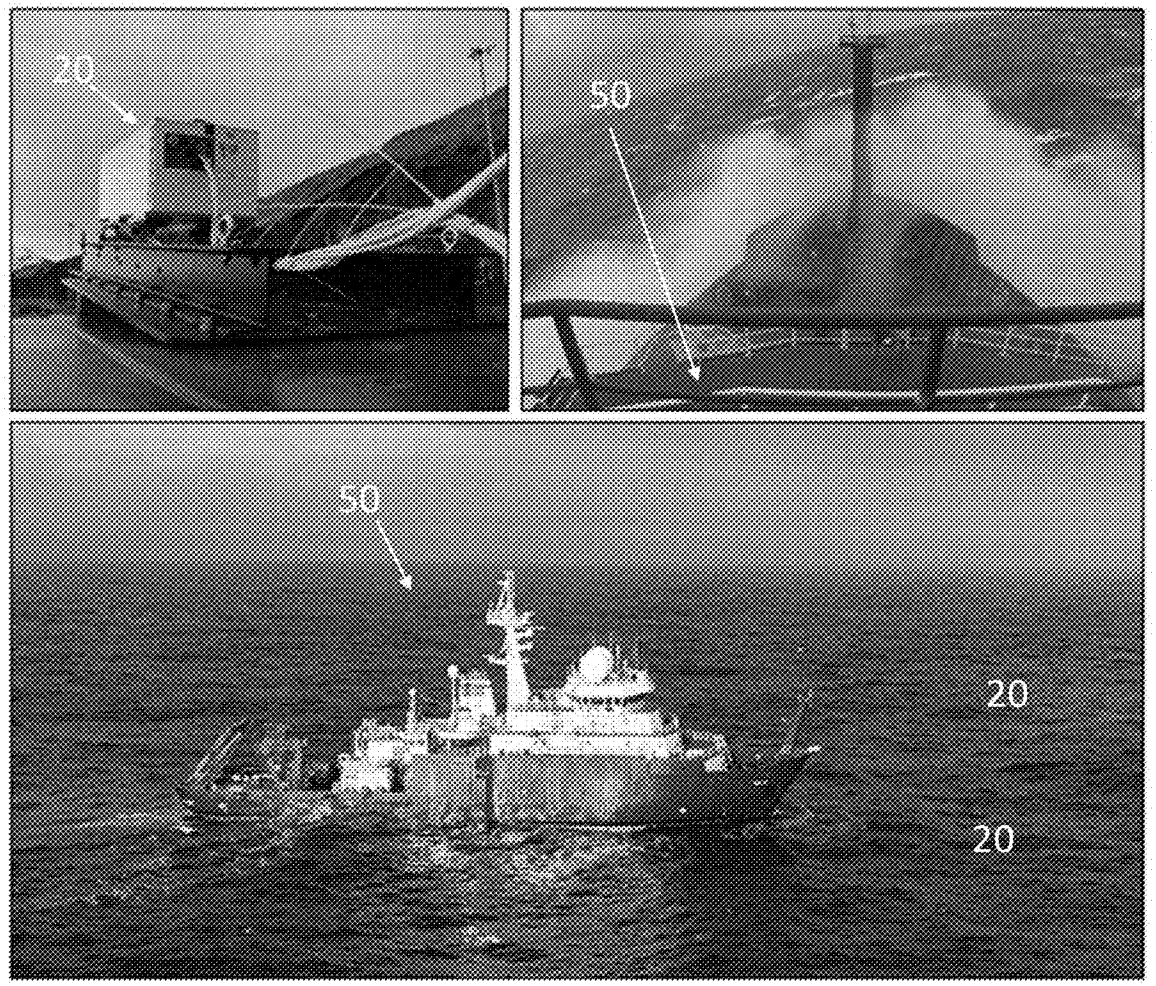
FIG. 1 illustrates an exemplary lidar acquisition device mounted on a ship in accordance with one or more disclosed aspects.

The aspects and features of the present aspects summarized above can be embodied in various forms. The following description shows, by way of illustration, combinations and configurations in which the aspects and features can be put into practice. It is understood that the described aspects, features, and/or embodiments are merely examples, and that one skilled in the art may utilize other aspects, features, and/or embodiments or make structural and functional modifications without departing from the scope of the present disclosure.

1. Overview

One or more aspects described herein describe the NRL shipboard lidar and an associated calibration procedure. One or more aspects described herein describe a novel lidar dataset of underwater bubbles, such as acquired by the lidar device. One or more aspects described herein describe the meaning of these lidar observations, the algorithm used and their current limitations. Aspects described here can be used to detect bubbles and their depth from the depolarization. Aspects described here can be used to determine and/or retrieve void fraction.

Disclosed embodiments provide for embodiments for detecting and deriving properties of underwater bubble clouds using lidar (e.g., shipboard lidar, or the like). Acoustic propagation is significantly impacted by rough, bubbly ocean surfaces (changes diffraction, attenuation, and scattering of acoustic energy; direction of propagation, increases transmission loss). Characterization of oceanic whitecaps and subsurface bubbles leads to improvements of acoustic propagation modeling. One or more aspects described herein can be used to derive the bubble void fraction and the depolarization with which bubbles can be detected (e.g., a bubble mask).

Lidar can contain bubble information but the inventors believe no one has developed an approach to extract the bubble information described herein from the lidar due to difficulty in obtaining measurements (e.g., in a storm).

One or more aspects described herein present here a novel method of deriving bubble characteristics from data of bubble profiles observed by lidar (e.g., shipboard lidar), such as in high wind conditions. One or more aspects describe herein describe cases encountered as well as the statistics of the data. One or more aspects described herein explain the meaning and application of these lidar observations. For example, lidar has the ability to provide simultaneous vertical information of both the atmosphere and ocean. As such, lidar data can provide the information of the bubble vertical distribution within the context of wave height and sea spray injection. Lidar use opens interesting possibilities for evaluating the air-sea interface.

One or more aspects described herein show that the depolarization of the bubble features comes from small angle multiple scattering and for this reason, the vertical depth is measured accurately with the shipboard lidar.

Whitecaps and bubbles have a strong and unambiguous depolarization signature. One or more aspects described herein can use this information as the base for a feature detection algorithm of ocean bubbles (a "bubble mask"). One or more aspects described herein show that a change of paradigm is necessary for the whitecap term embedded within the lidar equation for in-water laser light propagation.

One or more aspects described herein describe the void fraction retrieval and its accuracy. One or more disclosed embodiments provide for systems and methods that can provide the void fraction of underwater bubble clouds.

One or more disclosed embodiments provide for systems and methods that can discriminate between bubbles and background in lidar data. One or more disclosed embodiments provide for systems and methods that can determine the bubble depth of identified underwater bubble clouds.

One or more aspects provide for a method that may include first correcting from electronic artifacts and apply a set of signal correction. The altitude of the sensor can be used to regrid lidar profiles into a fixed reference. Once the signal is corrected, one or more aspects described herein provide for calibrating based on power units (e.g., Watts) and then into backscatter units (e.g., m-1·sr-1). A feature detection algorithm can run and can separate bubbles from non-bubble data. Additional correction can be made based on statistical properties (e.g., attenuation) of the bubbles and non-bubbles data. One or more aspects described herein provide for deriving, based on these corrections for example, the void fraction of the bubble cloud, injection rate of bubbles, and/or decay rate of diffused bubbles. Aspects describe herein provide for allowing collocation with other instruments.

2. Instrument Design

2.1. System Overview

The Naval Research Laboratory (NRL) Shipboard Lidar is one of the major assets of the NRL Ocean Sciences division at the NASA Stennis Space Center. It measures the elastic backscattering of laser light at 532 nm. The main data products are ocean backscatter coefficient, total attenuation coefficient, and degree of linear polarization (Gould et al. 2019). The lidar has been used on ship deployments continuously from 2013 to 2019 (East Sound in Washington state, Chesapeake Bay, Gulf of Maine, Atlantic ocean, Lake Erie, and Gulf of Mexico).

An electro-optic modulator can be used to modify the polarization of the laser light from circular to linear, and the receivers can be set to be sensitive to both polarization states. For each state of polarization, two receivers can measure the co- and cross-polarized backscattered return. Recently, the system was slightly modified for oil research (Gould et al. 2019) with the laser polarization kept linear. Two receivers measure the co-polarized backscattered light, one receiver measures the cross-polarized return and one receiver is sensitive to the fluorescence of oil with a relatively wide (50 nm) bandpass filter centered at 575 nm. The NRL Shipboard Lidar is designed to be mounted on the bow of research vessels, and in some cases, the laser may be pointed at the water at an angle between 15 and 20 degrees to limit the ocean surface backscatter intensity. It was mounted at an angle of 6.3 degree on the R/V Sikuliaq because the anticipated adverse mechanical conditions lead the inventors to design a much sturdier mount. The surface signal contribution at this lower angle was not an issue because of the rough ocean condition (e.g., roll of the ship and rough surface).

The lidar device was designed to be as compact as possible while ensuring enough structural robustness to enable deployment on a ship while underway. This sturdy design allows the system to sample ocean properties, even in the harsh environment of the open ocean. This was demonstrated without ambiguity during the 18 day deployment (Dec. 5, 2019 to Dec. 23, 2019) in the Gulf of Alaska in high winds and storm conditions, with wave heights recorded up to 17 meters.

FIG. 1 illustrates an exemplary lidar acquisition device 20 mounted on a ship in accordance with one or more disclosed aspects. The lidar acquisition device/system 20 (also referred to herein as the lidar or the like) can be set, mounted, or the like on a vessel 50 (e.g., a ship like the R/V Sikuliaq), such as shown in FIG. 1. In some embodiments, the device 20 may operate in an unmounted state and/or may be mounted to another type of object. The wave events may be determined based on an assessment or analysis of the captured lidar data itself. The crew reported that the lidar was under 6 feet of water three times due to large waves reaching the bow the night of the Dec. 11, 2019, while the lidar was not operating. It did not show any degradation of capabilities after this or any other wave events it experienced. In some cases, the device 20 may capture information (e.g., images) at regular intervals to capture wave events (e.g., to provide a representative sample of wave events). In some cases, the interval may range from about 12 per hour to a few dozen per hour.

2.2. Lidar System Description

Figure 2:
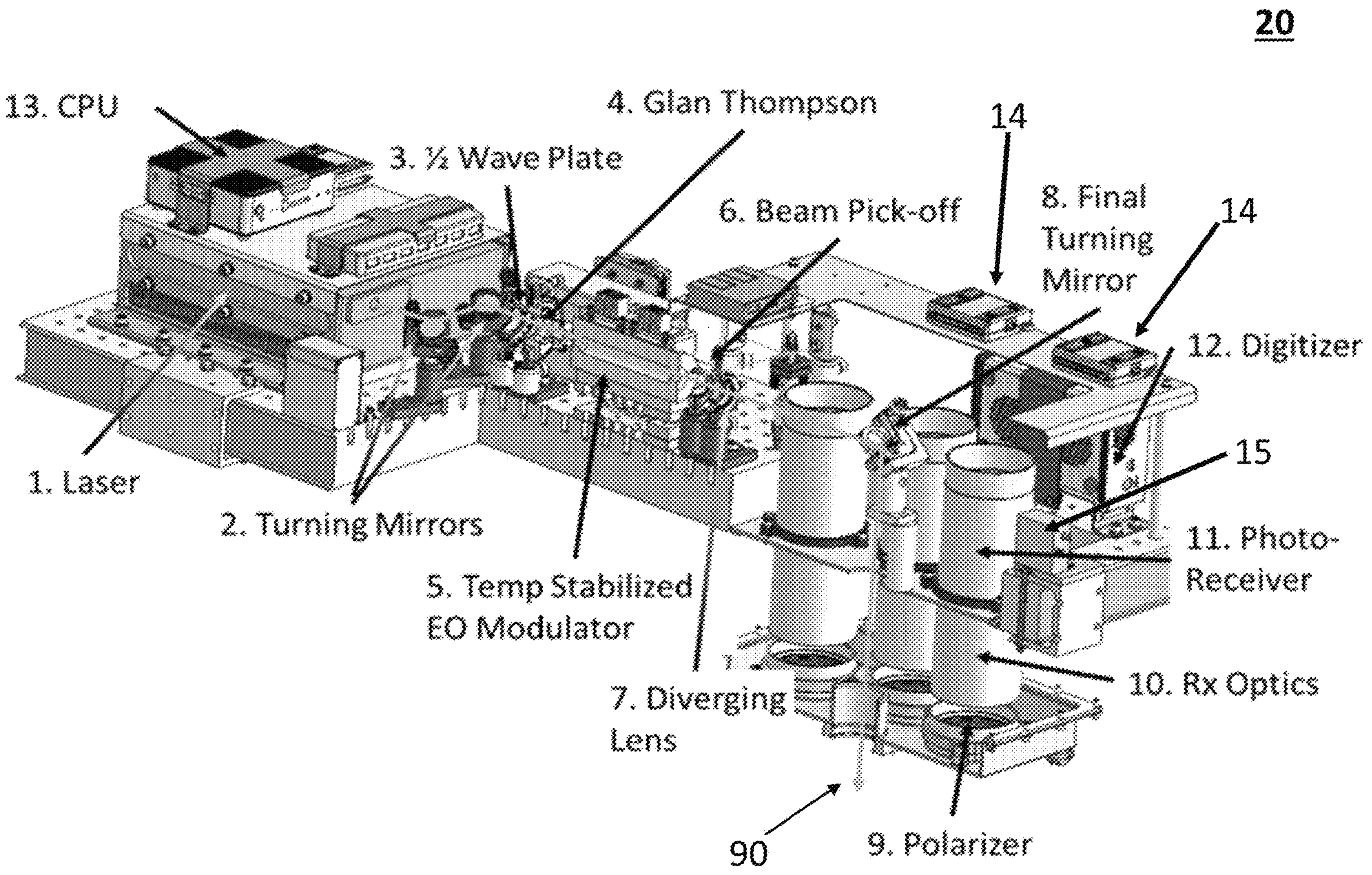
FIG. 2 illustrates an exemplary lidar acquisition device, in accordance with one or more disclosed aspects.

FIG. 2 illustrates the lidar acquisition device (and/or lidar system) 20, in accordance with disclosed aspects, and may include a laser transmitter 1, beam polarization optics (e.g., turning mirrors 2, ½ wave plate 3, Glan Thompson 4, temp stabilization Electro-Optic modulator 5, beam pick-off 6, diverging lens 7, final turning mirror 8, polarizer 9, RX optics/telescope 10, photo-receivers 11, digitizer 12, and control hardware 14. The receivers 11 have an eight-degree field of View (FOV). The 1 ns pulse width of the laser transmitter 1 combined with the 800 MHz digitization rate permits a vertical sampling of about 0.14 meters underwater while the 50 Hz sampling yields an along track resolution of approximately 0.02 to 0.1 meter. In order to provide sufficient overlap between the transmitted beam spread and detector FOV, the shipboard lidar 20 may be mounted at least 14 feet above the sea surface in this example, but may be placed at some other predetermined distance in other embodiments. In some embodiments, the Electro-Optic modulator 5 may be removed, which may, in some cases, lead to a reduction of the amount of electronic noise in the signal.

The transmitted laser beam path 90, which is transmitted by the laser transmitter 1 is shown in FIG. 2. The transmission of the laser beam 90 goes through an optical window situated in the center of up to six receiver units 11 (e.g., photo-receiver). Each receiver 11 includes a RX optics/telescope 10, which focuses the lidar return signal to a photomultiplier tube (PMT) comprised in the receiver 11, and the electrical signal from the PMT is connected to a digitizer 12 channel. In some cases, the receivers 11 may be identical, and in some embodiments, may have different polarizers 9 or/and optical filter (e.g., inside telescope 10) at the entrance aperture to allow detection of the polarization of interest (or wavelength for fluorescence). In some embodiments, there may be 6 receiver positions and the acquisition software may be developed for up to 6 channels which makes the system modular and reconfigurable. In some embodiments, there may be 4 receivers 11 and 2 digitizers 12 (with two channels each). In some cases, there may be other configurations and combinations.

In some cases, due to the proximity to the water surface, the signal to noise is typically higher than for airborne or spaceborne systems. Some characteristics of the transmitter 1 and receiver (e.g., elements 10 and 11) are in Table 1 and Table 2. A difference between this lidar 20 and most other operational systems is the high vertical resolution of the oceanic feature it can detect (e.g., about 14 cm underwater). Additionally, the low speed of the boat and relatively fast sampling rate creates an almost stationary measurement where the lidar does not move but the ocean feature evolves under it as a function of time. According to some aspects, it is quite complementary to airborne and spaceborne lidar observations.

A custom compression algorithm method created and implemented by NAWCAD allows the system to go beyond the 11 Effective Number of Bytes of the digitizer 12 and reach a dynamic range $>10^4$.

The data acquisition system 13 is designed to provide remote control and diagnostics of the lidar 20 while it is set on the bow of the ship 50 with no safe access. Additionally, the lidar 20 may be designed to run 24/7 even without possibility of manual adjustment or repair even during several weeks of boat deployment in storm conditions. In some embodiments, the parameters (PMT gains, gate timing, etc.) and/or control commands are sent to the lidar 20 from a master laptop computer coupled to the system 13 while the lidar system box stays sealed.

In some cases, a GPS/IMU unit 15 collects attitude and position information for each laser shot and added in real time to the lidar data stream.

TABLE I

NRL Shipboard Lidar transmitter specifications

| | |
|---|---|
| Wavelength | 532 nm |
| Pulse energy | 1 mJ |
| Repetition rate | 50 Hz |
| Ground spot spacing | 0.1 m (10 knots)<br>0.02 m (2 knots) |
| Beam divergence | 12 mrad (after beam expander) |
| Pulse width | 1 ns |

TABLE II

| NRL Shipboard Lidar receiver specifications | |
|---|---|
| Telescope diameter | 5 cm (6 units) |
| Field of view | 140 mrad |
| Optical filter bandwidth | 1 nm |
| Detector quantum efficiency | >20% |
| Detector dark current | 1 nA |
| Digitizer sample rate | 800 MHz |
| Vertical sampling spacing | 0.14 m (underwater) |
| Digitizer resolution | 14 bits |

3. Field Mission Research Objectives

The lidar was mounted on the bow of the R/V Sikuliaq from 4 Dec. 2019 to 23 Dec. 2019. This winter deployment in the Gulf of Alaska was in collaboration with the UNOLS cruise of the "Wave breaking and bubble dynamics" (Breaking Bubble) lead by Principal Investigator J. Thomson and funded by the National Science Foundation (NSF). The project goal is to understand the turbulence beneath waves breaking at the ocean surface. The dynamics associated with bubble plumes generated during the breaking process are a particular focus. P. I. Thomson invited the NRL researchers to bring the lidar 20 on the cruise. The NRL participation and contributions to this work was made in the frame of the NRL internal project IMProved Acoustic Transmission loss estimate through space lidar (IMPACT). The goal of this project is to derive the vertical properties of bubble clouds with lidar technology and use this information to better understand the ocean environment.

Overall data gathered include more than 113 hours of data at 50 Hz (around 20 M ocean profiles) than span different winds and wave conditions. This lidar dataset allows the inventors to understand the statistical occurrence of bubbles in the ocean and is, as far as inventors believe, the first published results of this kind.

4. Meteorological Conditions and Sea State

Figure 3:
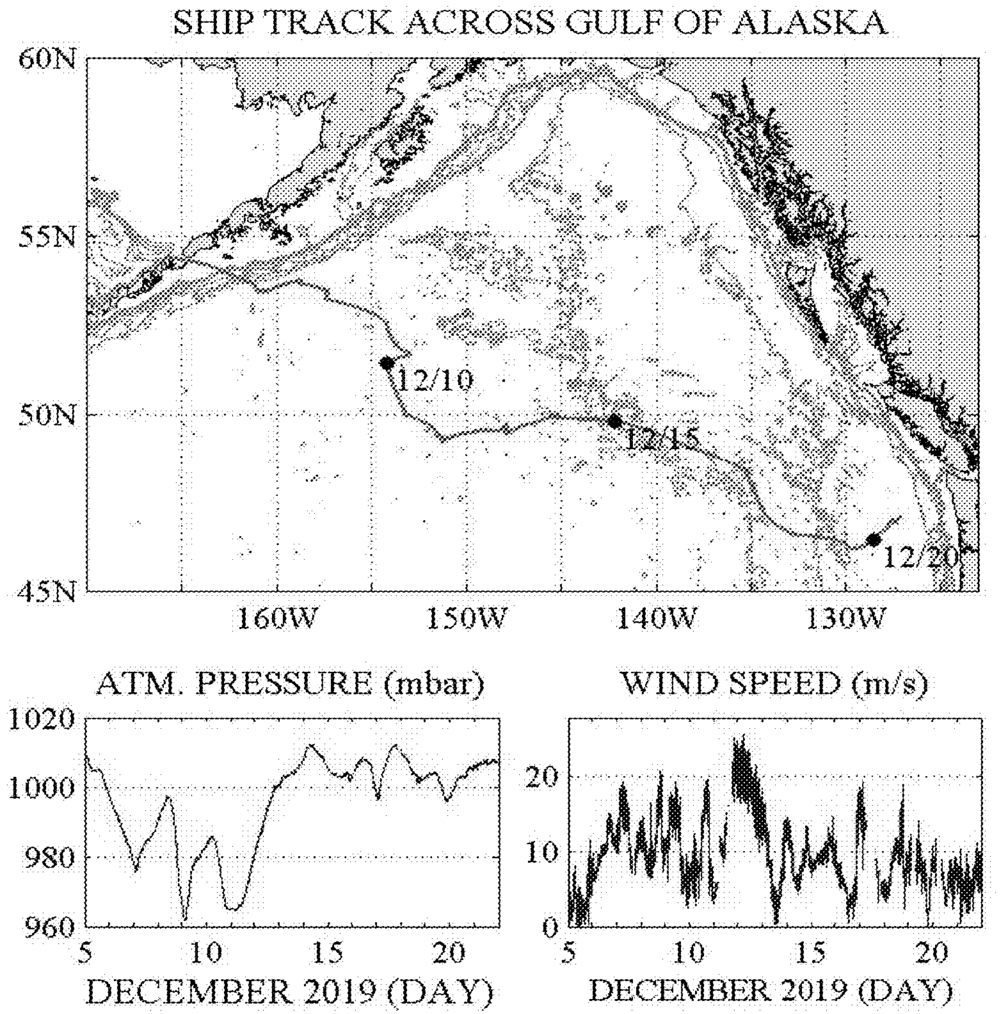
FIG. 3 illustrates an exemplary geographic track of the R/V Sikuliaq across the Gulf of Alaska, the pressure levels during the travel, and the wind speed during the travel, in accordance with one or more disclosed aspects.

FIG. 3 illustrates the geographic track of the R/V Sikuliaq across the Gulf of Alaska, the pressure levels during the travel, and the wind speed during the travel. As shown on FIG. 3, during the 18 day at sea exercise, the R/V Sikuliaq experienced several storm conditions associated with the passage of low pressure fronts below 1,000 hPa. The average wind speed value was 18.9 knots (±9.3) with a minimum of 0.1 and a maximum of 51.2 knots (with wind gusts up to 64 knots). Wave heights ranged from 3 to 10 m with wave events in the area as recorded by the Swift buoys (Thomson 2012, Thomson et al. 2019) up to 17 m.

The wind was coming mostly from West and South-West (average 216.08±64.44 degree). Water salinity, temperature and chlorophyll-a content were relatively stable at 32.14±0.14 p.s.u, 10.22±1.53° C. and 1.94±0.32 $mg \cdot m^{-3}$ respectively.

Figure 4:
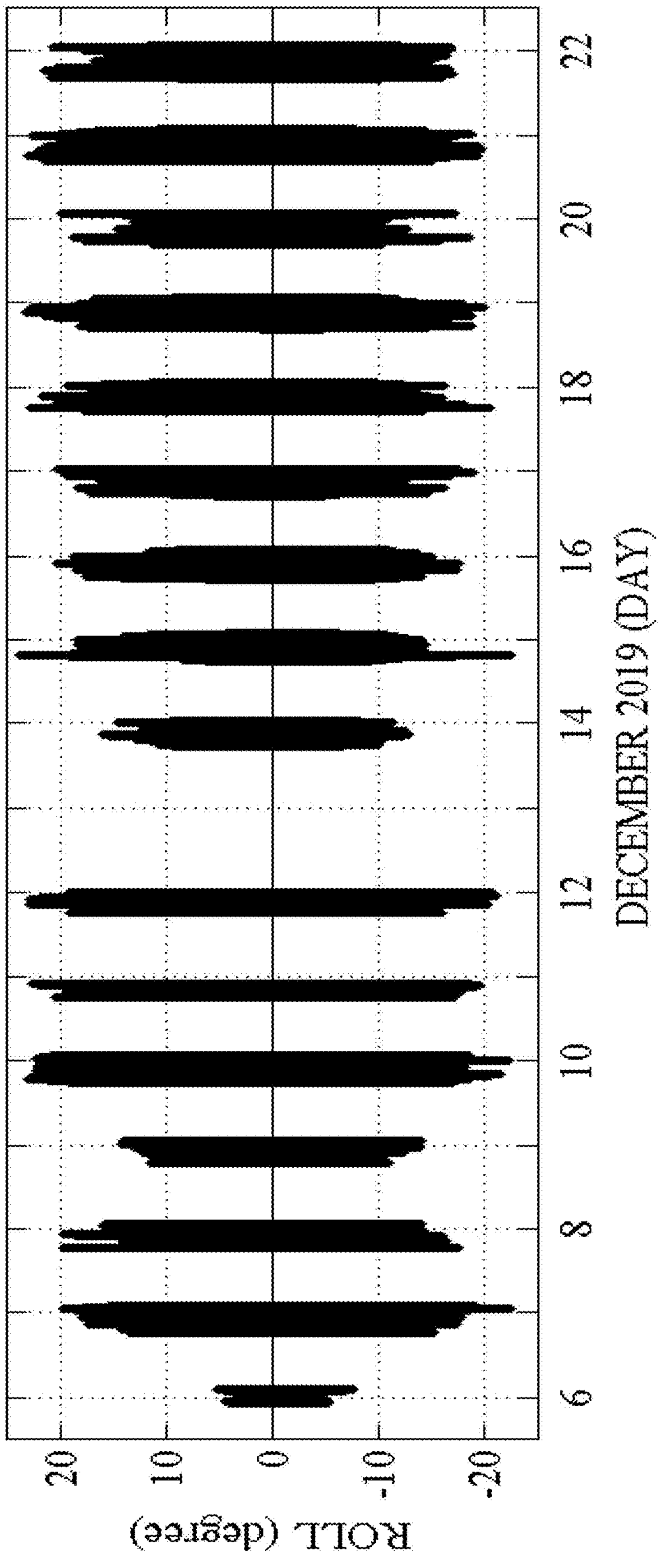
FIG. 4 illustrates an exemplary roll of the R/V Sikuliaq, in accordance with one or more disclosed aspects.

FIG. 4 illustrates the roll of the ship, the R/V Sikuliaq. In terms of shipboard conditions, the boat experienced regular 20 to 30 degree roll (FIG. 4) as the multidirectional wave systems made it difficult to find a stable heading for the ship. However, the conditions were ideal to find bubbles generated by breaking wave events due to the high wind speed (FIG. 3, bottom right).

Figure 5:
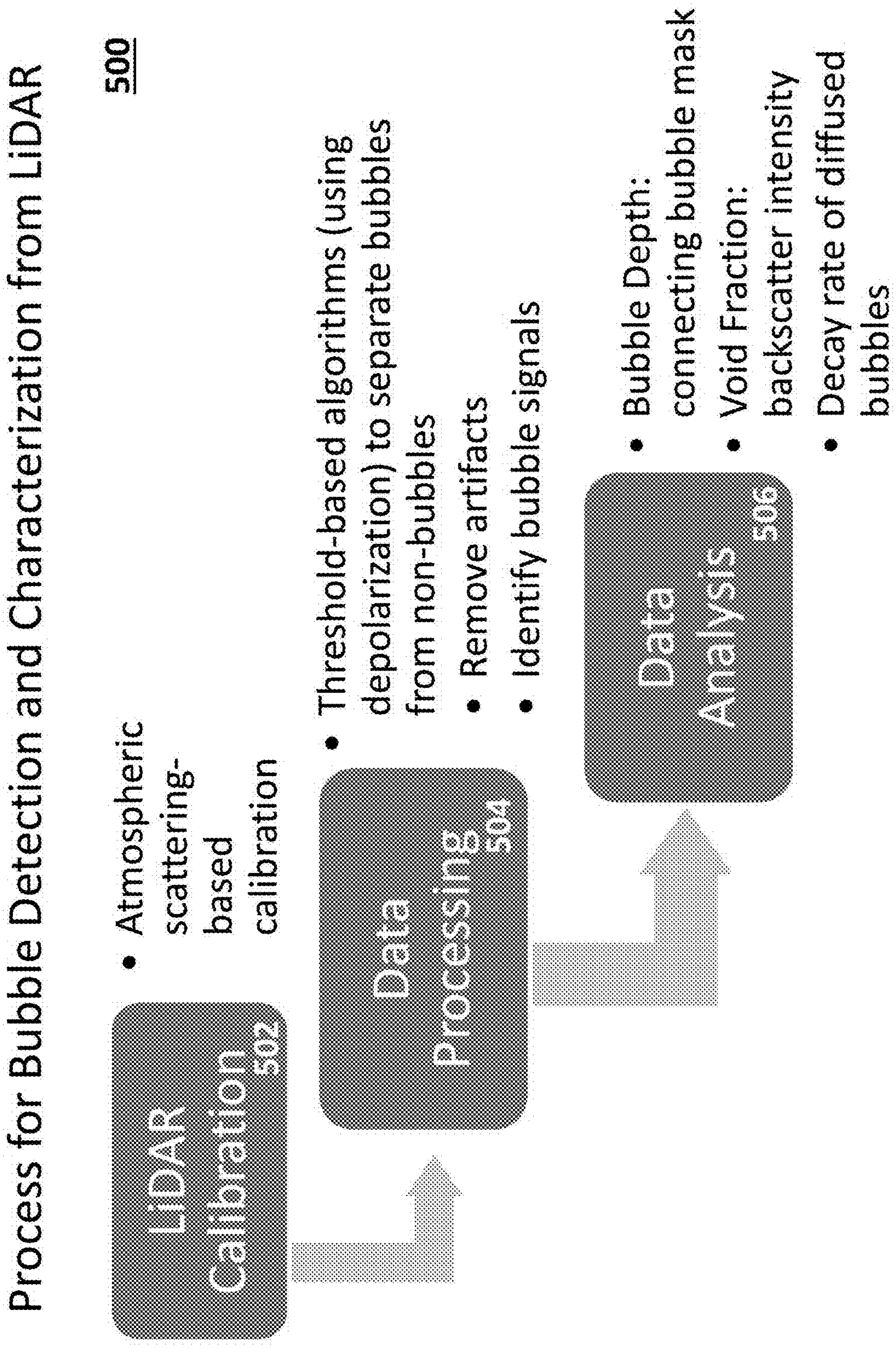
FIG. 5 illustrates an exemplary flow schematic diagram of an exemplary method for acquired lidar data, in accordance with one or more disclosed aspects.

FIG. 5 illustrates a flow schematic diagram 500 of an exemplary method for acquired lidar data in accordance with disclosed aspects. Each step is described here and is additionally described herein in other parts of the disclosure.

Step 502 may include lidar calibration. This step may include atmospheric scattering-based calibration, where the calibration of the lidar data is based on atmospheric scattering.

Step 504 may include data processing. This step may include threshold-based algorithms (e.g., using depolarization) to separate bubbles from non-bubbles. This step may include removing artifacts (e.g., linear depolarization larger than 1), identifying bubble signals, or the like. According to some aspects, after calibration, the bubble mask may be derived via a threshold on depolarization (e.g., used as feature detection). According to some aspects, a depolarization ratio larger than 0.015 (and less than 1) may be considered to be bubbles.

Step 506 may include analyzing data. This step may include determining bubble depth, which may be determined via connecting or incorporating the bubble mask. For example, depth may be determined via using the bubble mask with continuity for depth consideration. Continuity is the number of continuous data points below the water surface classified as bubbles. Bubble clouds may manifest as large increases of depolarization, which may increase with wind speed. This step may include determining a void fraction, such as via backscatter intensity. This step may include determining a decay rate of diffused bubbles. In some cases, bubble depth may be determined without continuity.

These steps described in flow schematic diagram 500 are described further herein, such as with respect to other figures.

Figure 6:
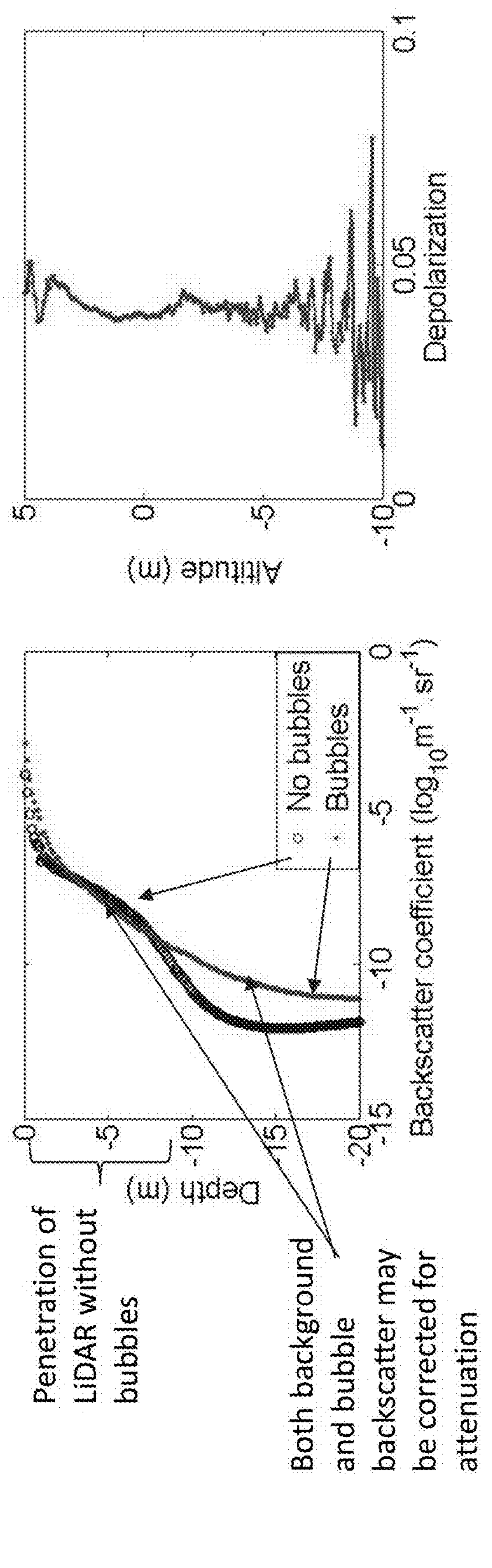
FIG. 6 illustrates an exemplary average backscatter and depolarization of bubbles for a 30 min sampling on 11 Dec. 2019, in accordance with one or more disclosed aspects.

FIG. 6 illustrates the average backscatter and depolarization of bubbles for a 30 min sampling on 11 Dec. 2019.

According to some aspects, there is a constant of proportionality between bubble void fraction and the lidar backscatter coefficient (Churnside et al 2010). Depolarization of the lidar signal is a function of the bubble size distribution for the shipboard lidar.

In some embodiments, the backscatter coefficient may be corrected for bubble attenuation and molecular background before the backscatter coefficient can be related to void fraction.

Because bubbles are spheres of air in the ocean, their scattering behavior can be calculated and theoretical relationships have been derived between bubble backscatter coefficient and void fraction (Churnside et al. 2010).

One or more aspects described herein analyze the statistical properties of the data with and without bubbles (based on the bubble mask). This allows correction of the bubble data from the contribution of water molecule scattering as well as from attenuation of water molecules and the bubbles themselves. This procedure provides the bubble backscatter coefficient from which one or more aspects described herein can retrieve the associated void fraction.

5. Data Calibration Procedure

One or more aspects described herein used both the atmospheric backscatter and the ocean surface as calibration targets. Because of the shipboard lidar's proximity to the ocean surface, one or more aspects described herein have to take into account the presence of aerosols in the atmospheric return of a shipboard lidar. Interestingly, one or more aspects described herein found that the use of the ocean surface calibration return as a calibration target is not trivial for the shipboard lidar, whereas it works very well for a space lidar (Josset et al. 2010a). The exact cause can require more investigation but preliminary analysis indicates that the slope of the waves varies so much that the reference for the mean square slope of the waves can be adjusted (i.e. the ocean surface return changes significantly between the two sides of a large wave). Inventors have never noticed this issue in the calibration of the CALIPSO lidar, which may be because of the larger laser footprint and because waves are statistically smaller than what was experienced during this cruise. This is the reason why one or more aspects described herein might not perform the calibration based on the ocean surface. One of the advantages of the shipboard lidar is the huge signal to noise ratio, as well as the vertical resolution.

The general principle of the atmospheric backscatter calibration procedure has been described in previous publications. It is based on Rayleigh scattering (Rayleigh 1871, Young 1982). For a shipboard lidar, the accuracy of this calibration is expected to be much lower than for example a space lidar which can use clear air in the upper atmosphere as a calibration target (Hostetler et al., 2006, Kar et al. 2018). One or more aspects described herein describe the specific of the methodology to try to limit the uncertainty due to aerosol contamination.

The backscatter of molecules is determined from the measurement of air temperature and pressure from the RV Sikuliaq. This is made by a fan-aspirated MET4A Meteorological Measurement Systems by Paroscientific, Inc mounted on the forward mast. The Pressure Accuracy is better than ±0.08 hPa and the Temperature Accuracy is better than ±0.1° C. Because there are so little variations of height in a shipboard lidar, this value is used directly as a reference to the lidar signal. In order to take into account the movement of the boat and the surface waves, the calibration is made with the average of lidar signal between 3.5 and 4.2 meter above the ocean surface. This is a good compromise to have enough data for the aerosol filtering procedure, far enough from the lidar but not too close from the ocean surface. In order to limit the influence of heavy sea spray events on the statistic, the calibration is made on profiles with an atmospheric backscatter coefficient value close from the median value for the whole file. Although this does not correspond to the minimum of aerosols, this ensure that one or more aspects described herein have enough data within the file considered for the calibration while lowering the amount of aerosol contamination. Due to the presence of aerosols, one or more aspects described herein anticipate that the accuracy of this calibration procedure is low and the ocean data are biased low by an unknown factor. Assuming the average aerosol optical thickness of 0.13-0.14 (Remer 2008) to be spread evenly within a 500 to 1000 m boundary layer and a lidar ratio of 20-25 sr (Dawson et al. 2015, Li et al. 2021), this can be a factor 4 to 8 (i.e. close from up to one order of magnitude of calibration error), such as if there are no surfactants. This should not affect the bubble mask but this is may influence the void fraction retrieval. The presence of surfactants is to be expected. In some cases, if surfactants have not been taken into account, and it may lead to error compensations and an overall error lower that this estimate.

6. Results and Discussion

The lidar data were taken while the boat was facing into the wind and maintained a forward speed of around 1 to 2 knots. As one or more aspects described herein show, the lidar simultaneously senses above and below the water surface. Therefore, it provides the information bubble depth and void fraction, as a function of the surface roughness (intensity of surface return) and surface height.

6.1 Lidar Depolarization

6.1.1 Multiple Scattering Considerations

As expected from (Churnside et al. 2014), bubble clouds have a large effect on the cross-polarization channel. The change of depolarization (ratio of cross-polarization to co-polarization channel) is much more noticeable than the changes in the co-polarization channel. This is interesting considering the signal intensity relates to the void fraction (Churnside et al. 2010).

Figure 7:
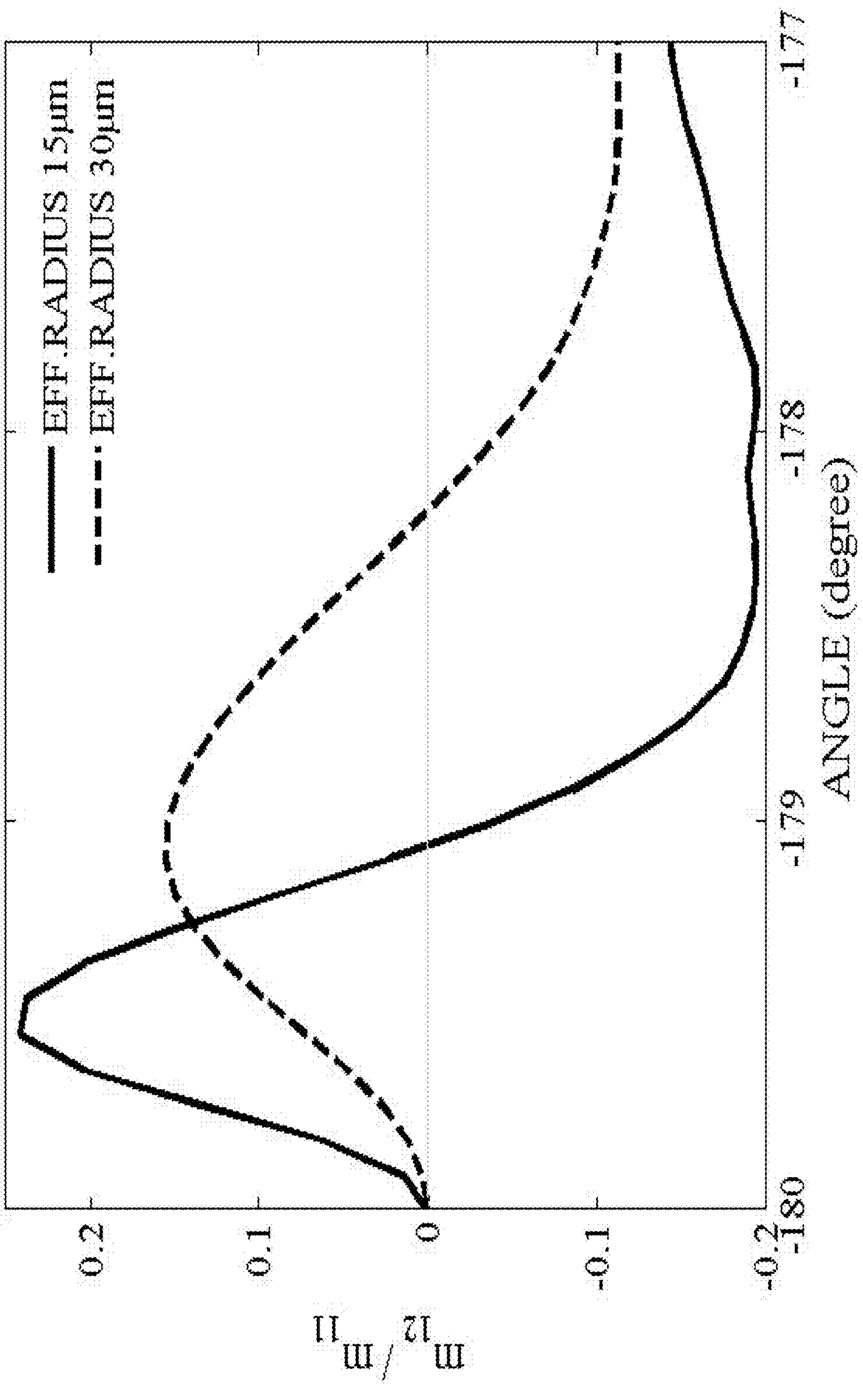
FIG. 7 illustrates an exemplary depolarization element of the Mueller matrix for spherical particles near the backscatter direction, in accordance with one or more disclosed aspects.

FIG. 7 illustrates the depolarization element of the Mueller matrix for spherical particles near the backscatter direction. The detection of depolarization of spherical particles in the backscatter direction implies multiple scattering of the lidar beam in an optically dense medium. For the NRL Shipboard lidar, because the system is relatively close to the target compared to other lidar systems, it might not detect light scattered back at exactly 180 degrees (i.e., the backscatter direction), and the exact angle may depend on the distance to the target. This can be shown by looking at the $M_{12}$ element of the Mueller matrix of spherical particles (Kokhanovsky 2003). As shown in FIG. 7, there is a larger variability of this element between 180 and 177 degrees. Note however that this single scattering calculation has very little meaning if the multiple scattering regime applies to the lidar observations as it may change the scattering geometry. However, it means that the NRL Shipboard Lidar should, within its sensitivity limits, be able to detect depolarization by bubble features optically thin enough to fall into the single scattering regime. In that case, observing the same bubble cloud with a change of the angle of observation due to the boat attitude or wave height change may provide information on the particle sizes.

In most instances, bubbles in the ocean are optically dense, and the single scattering considerations might not be relevant. In that case, an important matter to understand is which regime of multiple scattering the lidar observations fall into (Eloranta 1998, Hogan 2008). Because of the ambiguity of the time of the scattering event, the bubble vertical properties measured by the lidar become inaccurate in presence of wide angle multiple scattering. It is because side (large angle) scattering events are measured as if they were coming from a greater distance.

Wide angle multiple scattering light occurs when the width of the "footprint" (X) projected by the field of view of the receiver at the range of the target is on the same order as the transport mean free path (MFP) of light (Hogan 2008). In other words, the lidar can measure accurately the vertical extent of the bubble field only if $$X \ll \frac{MFP}{(1-\omega_0 g)}. \tag{1}$$

Figure 8:
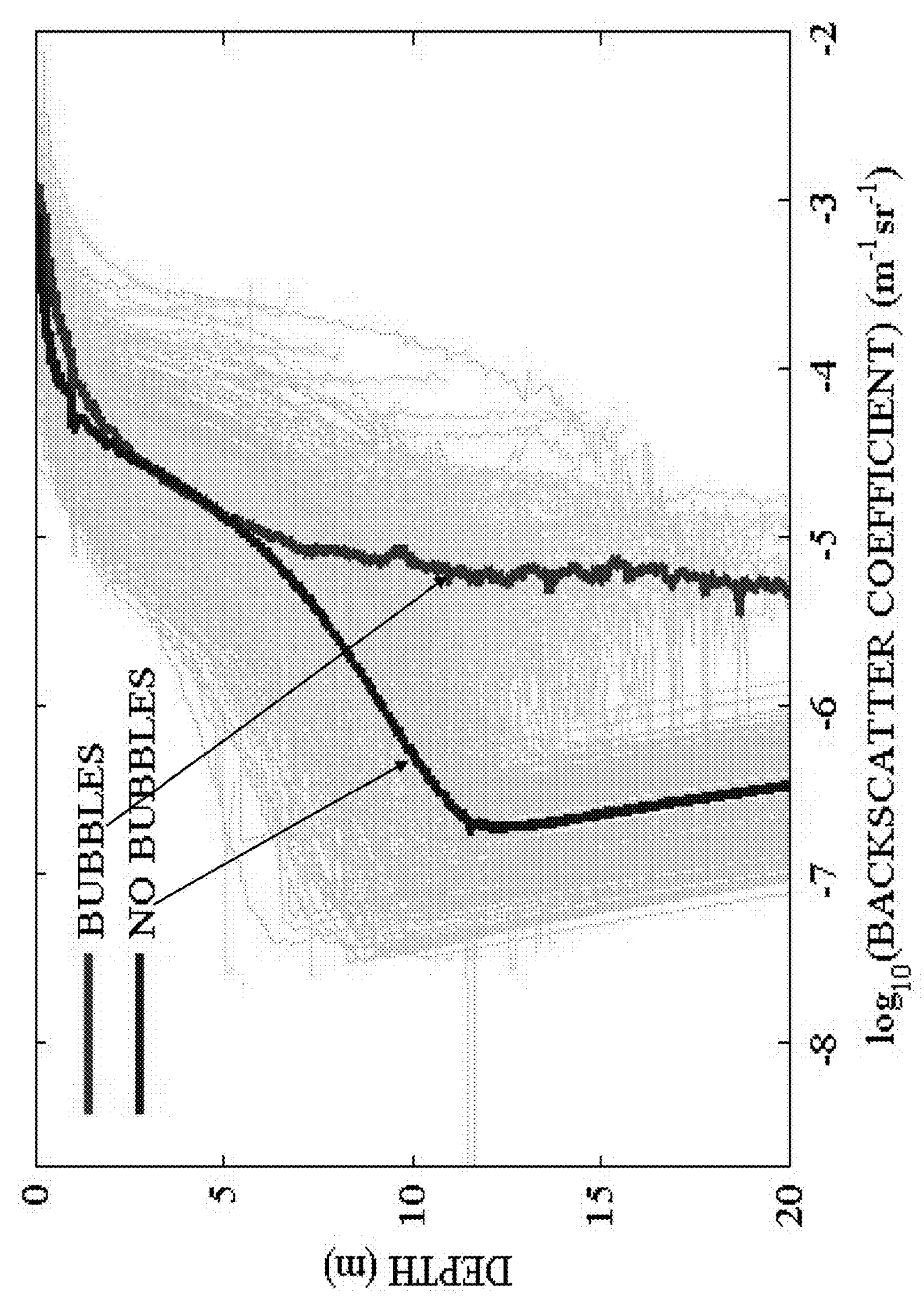
FIG. 8 illustrates an exemplary average backscatter coefficient of bubbles and bubbleless lidar profiles, in accordance with one or more disclosed aspects.

For air bubbles, the single scattering albedo coo can be approximated to be equal to 1 (Kokhanovsky 2003, Churnside 2010). The asymmetry factor g is approximately 0.8443 (Kokhanovsky 2003). The NRL Shipboard Lidar receiver has an angle of 8 degrees, which corresponds to a telescope footprint of around 1.2 m. This value varies slightly with the height of the waves and the attitude of the lidar (pitch, roll, yaw) and boat heave. On average, this means that the extinction due to scattering of the bubble cloud must be much lower than 5.35 $m^{-1}$. If one or more aspects described herein consider the profile of lidar backscatter coefficient, one or more aspects described herein can obtain the order of magnitude of the extinction coefficient due to the bubbles. This is shown in FIG. 8, which illustrates the average backscatter coefficient of bubbles and bubbleless lidar profiles. Even if the backscatter itself is expected to decrease as a function of depth as less and less bubbles reach these levels, the profile is monotonic enough that that the average slope provides the right order of magnitude for this coefficient. Note that even if the signal in bubble stays valid down to 20-30 meters (see section 6.2 and 6.3), it can be shown from FIG. 8 that the good quality of the backscatter signal for clear water is limited to a depth of 5-10 meters. There is no obvious geophysical reason to explain the change of backscatter coefficient slope around 5 meters and 12 meters. The increase of the backscatter coefficient as a function of depth (below 12 meters) is for sure a signal artifact.

The average slope of the logarithm of the backscatter coefficient is −0.24 $m^{-1}$ which corresponds to an extinction coefficient of 0.24 if one or more aspects described herein assume a multiple scattering coefficient of 0.5 (Eloranta 1998, Josset et al. 2012). This is significantly below the threshold to create wide angle multiple scattering even if using a different multiple scattering coefficients. The theoretical maximum of the multiple scattering coefficient should be close to 0.1 for full isotropization of light polarization in dense medium (Xu and Alfano 2005, Hu et al. 2006). As a side note, the 90 m footprint of the CALIPSO lidar implies that this system is well within the wide-angle scattering regime for underwater bubble clouds.

Concerning Small Angle Scattering, Following Hogan 2008, the Criteria is $$MFP\frac{\lambda}{\pi a} \lesssim X. \tag{2}$$

For the MFP corresponding to our observations, all bubbles with radius >0.5 μm are in the small angle scattering regime. Although the exact number of the smallest bubbles is typically not measured by acoustic sensors, a peak of the bubble size distribution around 10 to 30 μm is a standard assumption (Vagle and Farmer 1991, Kokhanovsky 2003). The tank experiment conducted in the breaking wave tank of the littoral high bay of the Laboratory of Autonomous System Research (Wang et al. 2022) seemed to peak around 1-2 μm based on acoustic resonance estimates so even these artificially generated wave conditions can fall under this scattering regime.

6.2 Maximum Penetration Depth

Figure 9A:
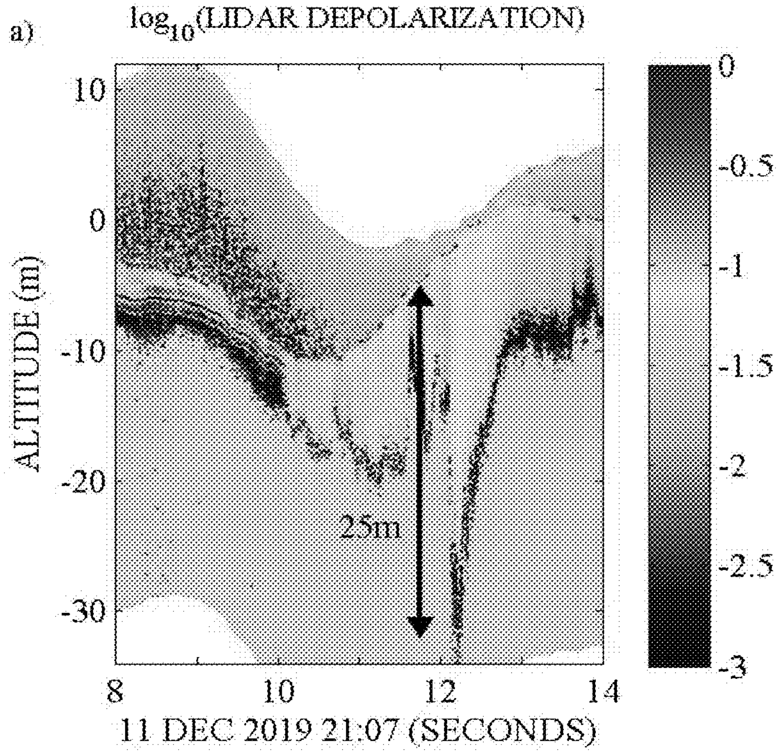
FIG. 9A illustrates an exemplary the depolarization of the lidar signal for an example case of bubble depth, in accordance with one or more disclosed aspects.
Figure 9B:
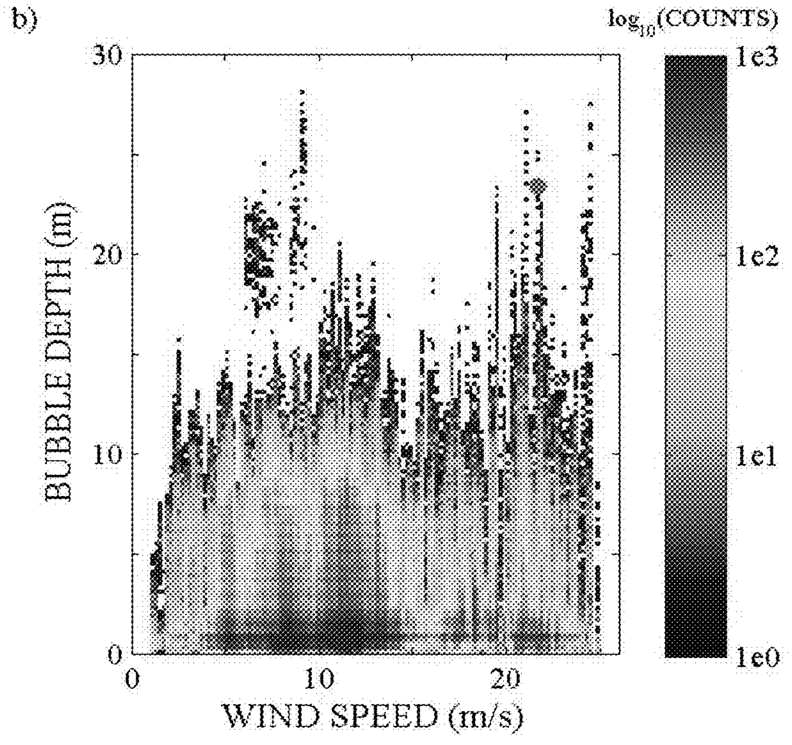
FIG. 9B illustrates an exemplary statistic of bubble depth from the bubble mask as a function of wind speed, in accordance with one or more disclosed aspects.

FIG. 9A illustrates the depolarization of the lidar signal for an example case of bubble depth. Green features are bubbles and blue features the ocean (bubbleless) water. FIG. 9B illustrates the statistic of bubble depth from the bubble mask (e.g., features going from the surface to some depth) as a function of wind speed. Because the NRL shipboard lidar observations fall into the regime of small angle multiple scattering one or more aspects described herein can retrieve the vertical extension of the bubble field with a limited attenuation. One or more aspects described herein describe the detail of the bubble feature detection in section 6.3. It may be based on the fact that bubbles depolarize the lidar signal quite significantly, which may be shown in FIG. 9A. The bubble mask allows to quantify the maximum penetration depth of this system in bubble clouds. As shown in FIG. 9A and FIG. 9B, lidar penetration depths over 25 m in bubble clouds are part of this dataset. Most of the bubble cloud observations have an extension between 0 and 10 meters. The observed bubble depth might not quite reach 30 m. Because of the apparent low occurrences of these deep clouds and the novelty of the bubble mask, the data represented in FIG. 9B might not allow discrimination between a limitation of the lidar sensitivity or a physical limitation of bubble injection processes.

6.3 Bubble Feature Detection

Figure 10:
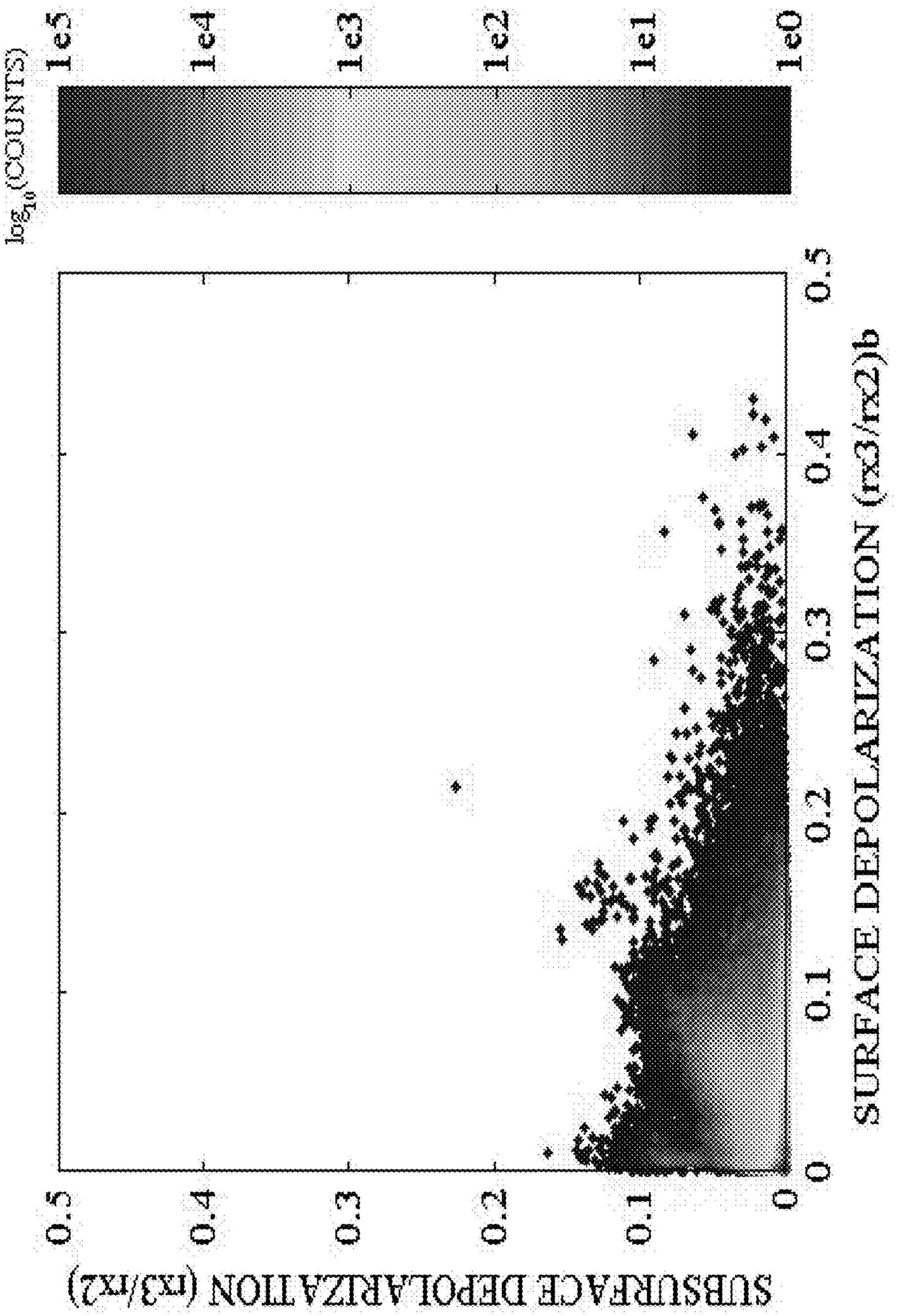
FIG. 10 illustrates an exemplary depolarization of the subsurface signal as a function of the depolarization of the surface signal, in accordance with one or more disclosed aspects.

Because whitecaps and bubbles have a clear depolarization signature, a depolarization intensity threshold can be used to create a feature detection algorithm and study the distribution of their vertical properties. One or more aspects provide a method and/or algorithm based on the dataset shown in FIG. 10, which illustrates the depolarization of the subsurface signal (higher for extended bubble clouds) as a function of the depolarization of the surface signal (higher for whitecaps). The continuum of observations can be separated in four broad domains.

Figure 11:
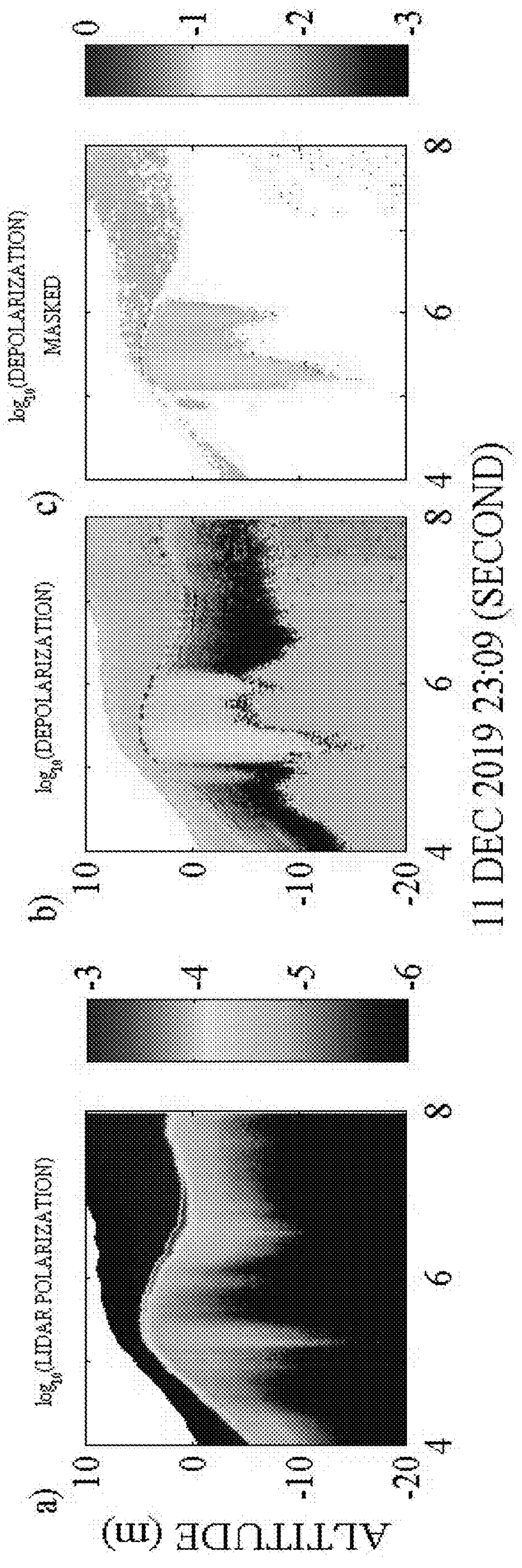
FIG. 11 illustrates an exemplary bubble mask results, in accordance with one or more disclosed aspects.

For the bubble mask, one or more aspects described herein used a threshold on depolarization as defined by the ratio of the cross-polarization channel on the co-polarization channel. After removal of some detection artifact (mostly data with linear depolarization larger than 1), only the data with depolarization ratio larger than 0.015 are considered to be bubbles. To determine the bubble depth, one or more aspects described herein also include an element of continuity. The bubble depth correspond to the number of continuous data point below the water surface and which depolarization value are above this threshold. This removes some false positive which manifest as isolated points due to the noise. The results of the bubble mask are illustrated in FIG. 11. As shown, the intensity and polarization features are clearly different. Also shown is that there remain false positive above the ocean surface (which is the marked yellow/red curved on the intensity, left of FIG. 11). These false positive are removed when the bubble depth is calculated as they are not a continuous structure below the ocean surface. The conical structures of bubbles from the depolarization are qualitatively similar to previous studies of bubble created by breaking waves (Novarini et al. 1998, Derakhti and Kirby 2014).

Figure 12:
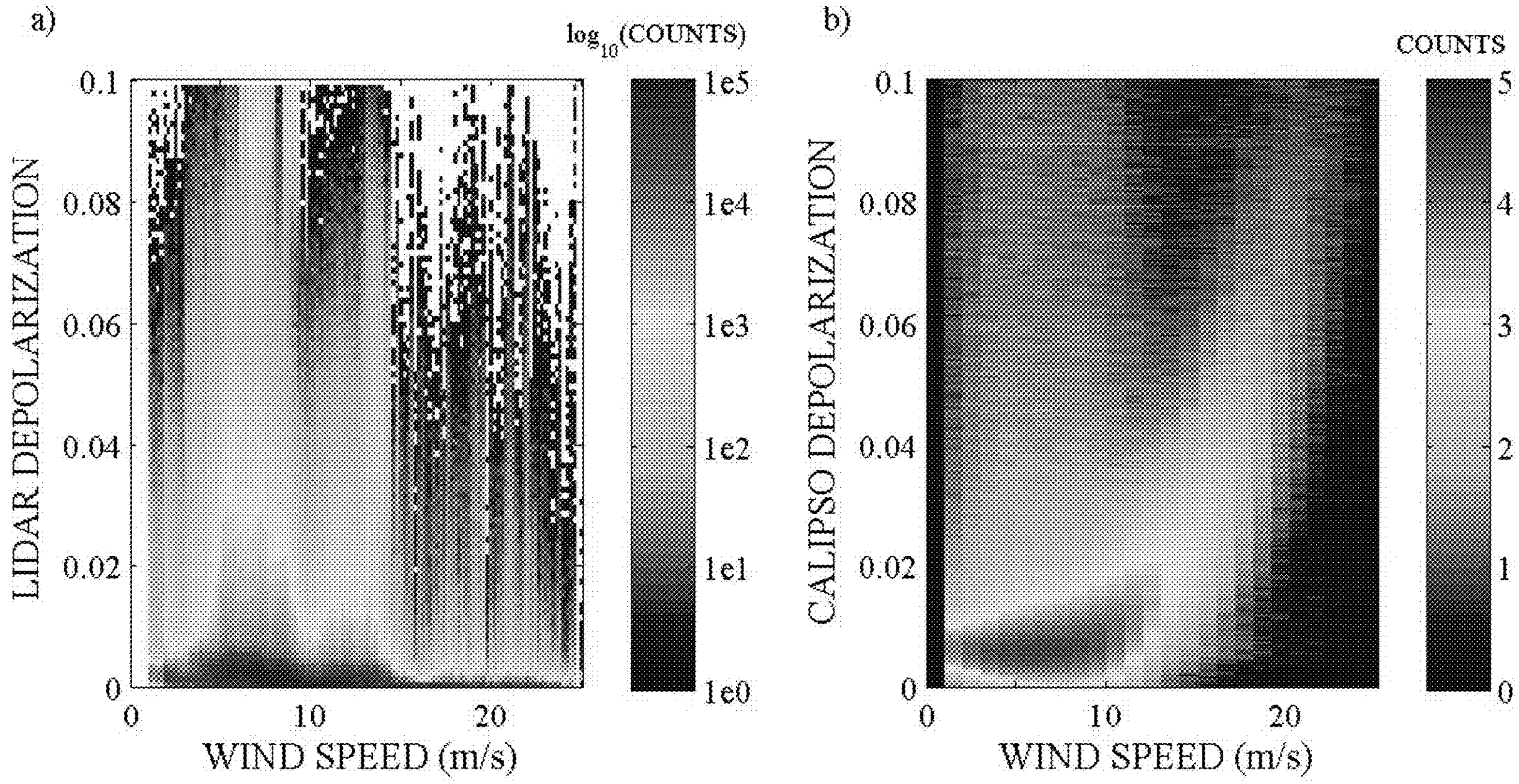
FIG. 12 illustrates an exemplary lidar depolarization as a function of wind speed and the CALIPSO lidar depolarization as a function of (AMSR-E) wind speed, in accordance with one or more disclosed aspects.

FIG. 12 illustrates the NRL Shipboard Lidar depolarization as a function of wind speed and the CALIPSO lidar depolarization as a function of (AMSR-E) wind speed. From the analysis of the depolarization as a function of wind speed, it may be that the lidar return signal represents a bubble to bubble-less ocean continuum (FIG. 12). The lidar depolarization background is increasing with wind speed and bubble clouds manifest themselves as large spikes in the depolarization. FIG. 12 (right) shows the same parameters measured with the space lidar CALIPSO at global scale and during 5 years (daytime measurements). Interestingly, starting at 10 m/s the space lidar detects only features with high depolarization. In order to increase the number of observations at high wind speed one or more aspects described herein only removed here data that contained stratospheric features and liquid water clouds. It is very interesting that CALIPSO does not detect much signal at low polarization when wind speed increases. It could be related to geophysical differences (winter in the Gulf of Alaska vs global scale)

or something instrumental related to the larger scale of the laser and telescope footprint (70 m and 90 m, respectively). It might not be a likely explanation as it can mean that statistically speaking, there is always a patch of whitecaps in the ocean inside a randomly sampled 70 m radius when the wind speed is over 10 m/s. Bubble everywhere has been proposed as a possible explanation of the puzzling relationship between the steepness of waves and wind speed (Munk 2009).

6.4 Whitecaps Contribution in the Lidar Equation

Figure 13:
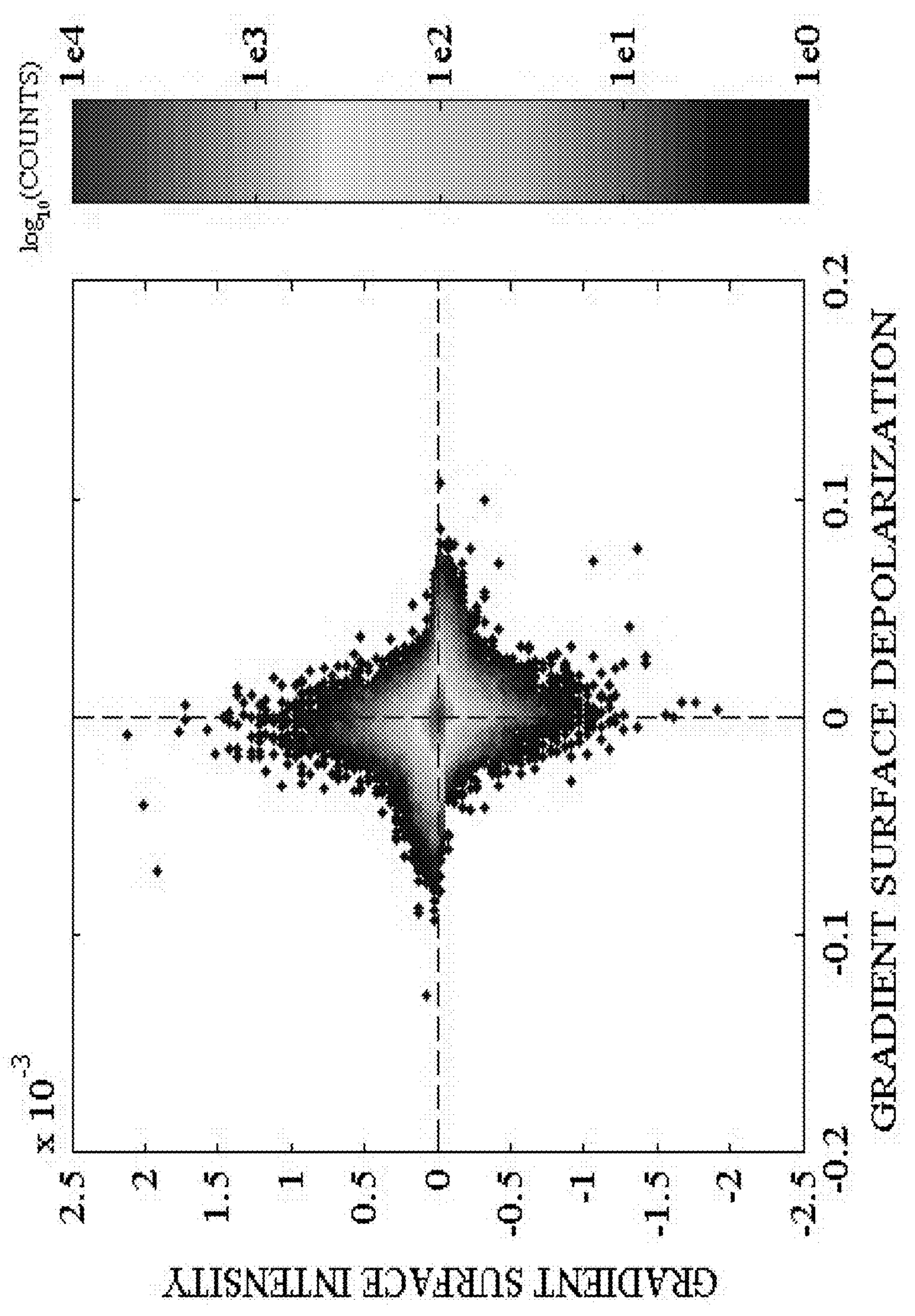
FIG. 13 illustrates an exemplary gradient of the surface intensity as a function of the gradient of the surface depolarization, in accordance with one or more disclosed aspects.

FIG. 13 illustrates the gradient of the surface intensity (co-polarization channel) as a function of the gradient of the surface depolarization. Interestingly, no strong gradient of the surface return intensity is associated with the presence of the bubbles clouds. Note that a moderate increase of the signal intensity is still present which allows the inventors to calculate a void fraction (see section 6.5). It appears more clearly in an experiment that was conducted in the breaking wave tank of the NRL Laboratory for Autonomous System Research in September 2019 (Wang et al. 2022). The smooth transition between bubble and bubble-less ocean is a new result as the current lidar equation formalism (Menzies et al. 1998, Josset et al. 2010b) creates a clear boundary between the specular reflectance of the ocean and the reflectance of whitecaps. It can be seen from Eq. 2 and Eq. 21 of Jos set et al. 2010b that the specular reflectance term may become close from 0 as the whitecaps coverage fraction (W in these references) converges towards 1. If this formalism was correct, a clear gradient of intensity can be associated with the strong depolarization events of bubbles. As shown in FIG. 13, there is no correlation between the horizontal gradient of the ocean surface return and the gradient of surface depolarization (correlation coefficient is −0.1871) so a continuum of states can be more appropriate to describe the physics of bubbles in the ocean.

6.5 Void Fraction Retrieval

The relationship between lidar backscatter coefficient and void fraction has been derived by (Churnside 2010). The link is a multiplication constant and the lowest value is for bubbles without surfactant. Before one or more aspects described herein can apply this multiplicative constant to the NRL lidar, one or more aspects described herein can correct the data from attenuation and separate the contribution from bubbles to water molecules.

In order to do so and for a profile with bubbles, perform the following.

Using the bubble mask, one or more aspects described herein select all the profiles without bubbles (so this includes water molecules and biology). One or more aspects described herein then determine the extinction from the signal decrease as a function of depth from the average profile. For this dataset, the average extinction is around 0.1083 m-1 which is consistent with the water chlorophyll content and the diffuse attenuation of previous studies (Morel and Maritorena, 2001).

Figure 14:
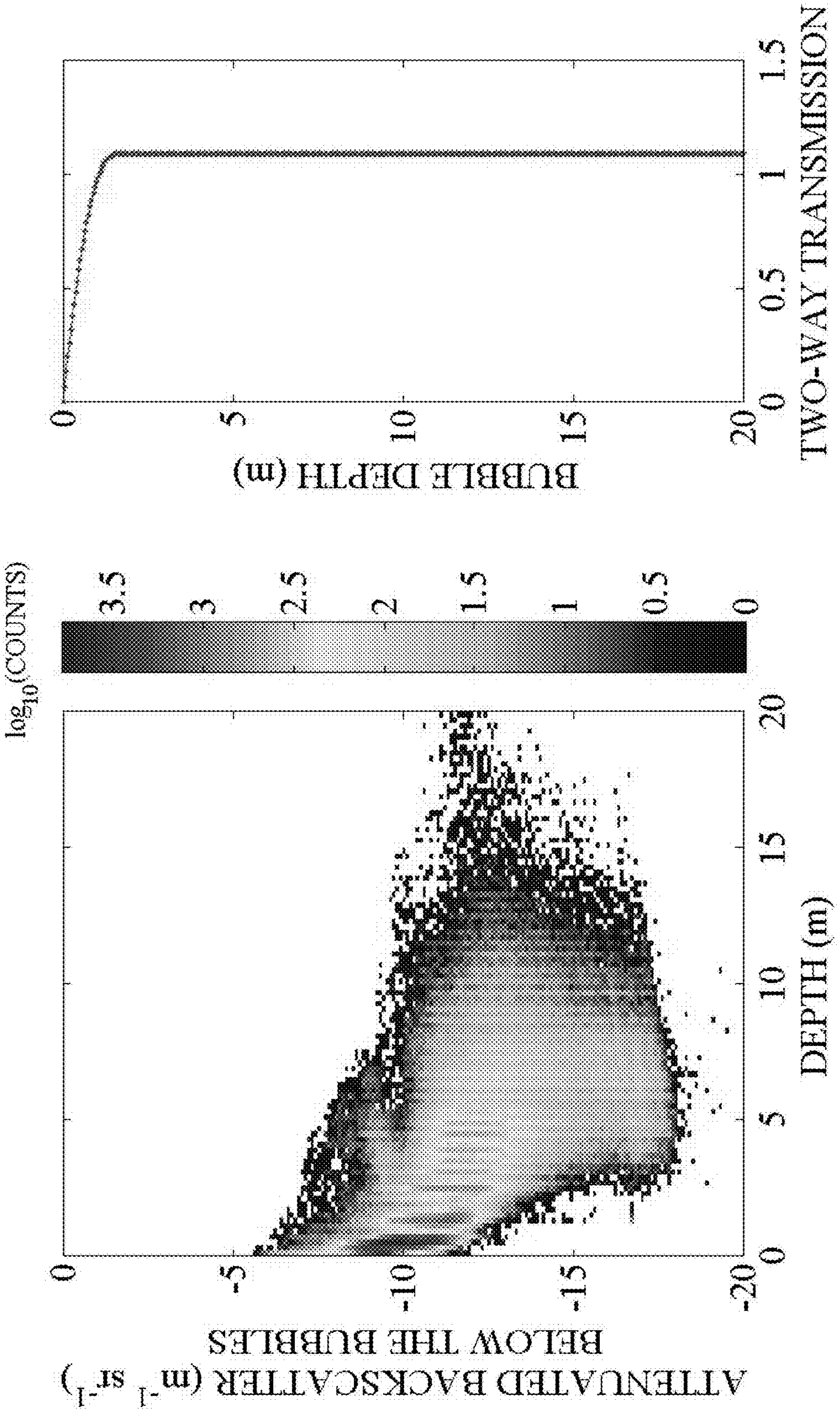
FIG. 14 illustrates an exemplary attenuation value, in accordance with one or more disclosed aspects.

The backscatter intensity just below the bubble clouds can be used to determine the attenuation of scattering by water molecules. Specifically, for each profile, one or more aspects described herein store the logarithm of the backscatter intensity 0.47 m below the lowest depth as determined by the bubble mask (average of the 0.7 m of signal). Going slightly below the bubble cloud minimize the likelihood to still have bubbles in the signal and allow the inventors to measure the backscatter of water molecules attenuated by the bubble cloud. This attenuation value is shown in FIG. 14. The data suggests that there could at least two or three regimes of attenuation of the bubble clouds (discontinuity of high attenuation around 4-8 m and low attenuation around 2-6 m). One or more aspects use the retrieved extinction as low as 1.5 m which correspond to the highest number of data. In addition, only one attenuation regime may exist below this depth in FIG. 14. Below this value, one or more aspects described herein assume that the two-way extinction caps at 1.0892. This value is consistent with the decay of the logarithm average backscatter of bubbles between 2 and 5 meters. This is consistent with less attenuation as the bubble density becomes lower.

Once both the bubble profiles are corrected from the total extinction, the average water molecules backscatter coefficient can be removed to retrieve the bubble backscatter coefficient and the associated void fraction.

There may be uncertainties due to the calibration coefficient and the lack of knowledge of the bubble surfactant. However, due to error compensation (i.e. the bias in these two factors partially compensate each other), one or more aspects described herein anticipate that the overall effect on the void fraction retrieval is a bias that cannot be higher than the calibration bias.

Figure 15:
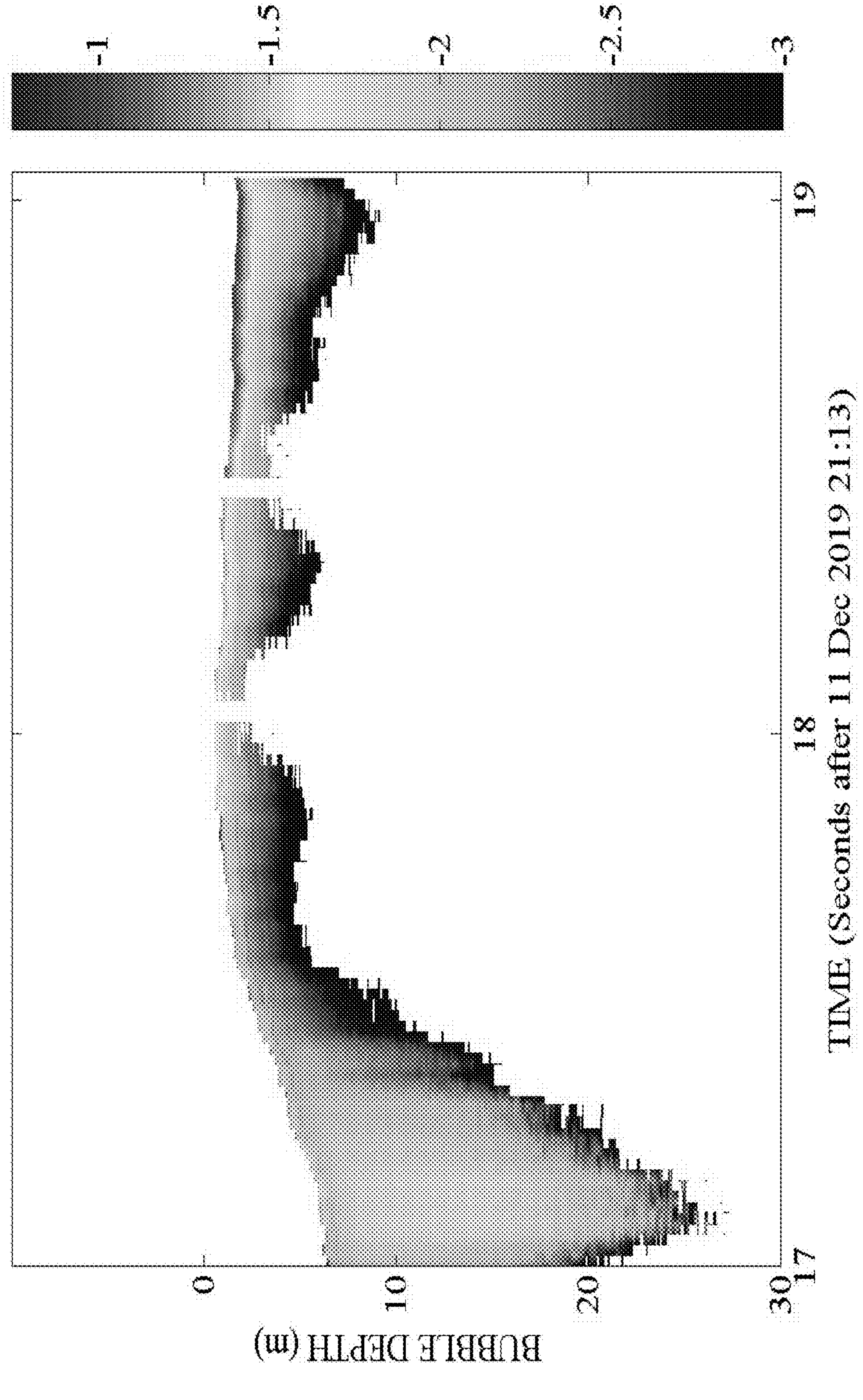
FIG. 15 illustrates an exemplary void fraction determination, in accordance with one or more disclosed aspects.

An example of the void fraction retrieval is shown in FIG. 15 for the data of Dec. 11, 2019 at 21:13:00Z. Interesting patterns emerge as all bubble clouds have different properties. The bubble clouds on the left (around second 17) has a much lower value of the void fraction at the surface than the bubble cloud observed a few seconds later (around second 19). This could imply that the bubble cloud on the left is older than the bubble cloud at the right of the figure.

The void fraction estimates depend on several algorithms which are either new or newly applied to the NRL shipboard lidar. This includes the bubble mask, the calibration procedure and the correction for attenuation. One or more aspects described herein can be applied to the whole shipboard lidar dataset (most of them without bubbles but with phytoplankton/zooplankton layers). This can provide further insight into the domain of validity of these algorithm as well as the associated uncertainty.

This work allows the inventors to determine the link between several bubble properties and the lidar measurements, such as the link between the bubble properties (e.g., bubble depth, void fraction) and the integrated lidar depolarization. This may allow estimates of bubble properties measured by a space lidar (CALIPSO). Aspects herein can be used to provide global scale bubble depth maps, which can help with sea missions and naval operations, for example.

One or more aspects described herein show that there is an intrinsic difference between passive sensors observations of the bubble field in real ocean conditions and what is detected by a lidar system which has the capability to penetrate the water surface and observe the whitecaps and various intensity of spray. Specifically, the water surface scattering properties which come from the statistic of the wave slope distribution might not exhibit drastic changes at the boundary between the bubbleless part of the ocean and waters with either whitecaps or extended bubble clouds. More generally, from the lidar perspective, the ocean manifests a continuum of features that appear above or below the water surface.

Figure 16:
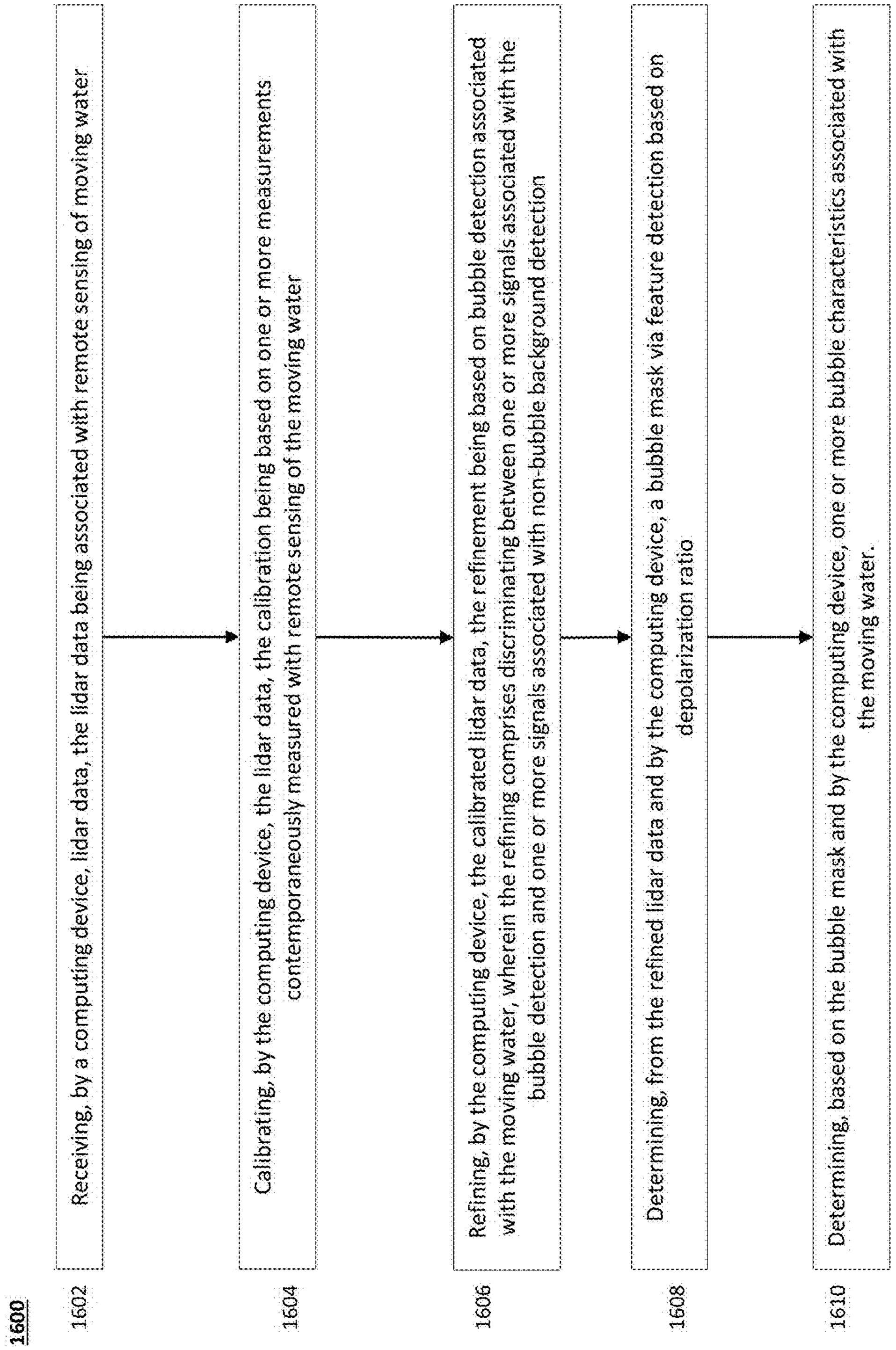
FIG. 16 illustrates an example method, in accordance with one or more disclosed aspects.

FIG. 16 illustrates an example method 1600, in accordance with one or more disclosed aspects. Step 1602 may include receiving, by a computing device (such as the one described in FIG. 17), lidar data, the lidar data being associated with remote sensing of moving water. Step 1604 may include calibrating, by the computing device, the lidar data, the calibration being based on one or more measurements contemporaneously measured with remote sensing of the moving water. Step 1606 may include refining, by the computing device, the calibrated lidar data, the refinement being based on bubble detection associated with the moving water, wherein the refining comprises discriminating between one or more signals associated with the bubble detection and one or more signals associated with non-bubble background detection. Step 1608 may include determining, from the refined lidar data and by the computing device, a bubble mask via feature detection based on depolarization ratio. Step 1610 may include determining, based on the bubble mask and by the computing device, one or more bubble characteristics associated with the moving water. One or more steps may be repeated, added, modified, and/or excluded.

One or more aspects herein have shown that a lidar is an ideal tool to obtain information of the bubble environment. The bubbles create a strong depolarization which is unambiguous and the lidar provides simultaneously the context of the air-sea interface (surface height). The void fraction retrieval uncertainty is typical of backscatter lidar limitations (calibration accuracy, attenuation correction, scattered refractive index). Bubble have the advantage to show a very strong scattering signature and there are physical limits that bound the void fraction retrieval. According to some aspects, void fraction cannot be larger than 1. The void fraction is currently used at inputs for acoustic propagation models. The lidar bubble methods described herein can be used in wave model bubble parameterization. The lidar bubble methods described herein can be transferred to the space lidar (NASA CALIPSO).

According to some aspects, one or more disclosed embodiments may have one or more specific applications. Lidar use opens interesting possibilities for evaluating the air-sea interface. For example, disclosed aspects may be used for search & rescue, for implementing and/or developing a mission route plan associated with operating a vehicle, aircraft, vessel, and/or the like. According to some aspects, one or more disclosed aspects may be used to facilitate a water-based operation. In some cases, one or more disclosed aspects may be used to facilitate a strategic operation, which can include a defensive tactical operation or naval operation. According to some aspects, acoustic propagation is significantly impacted by rough, bubbly ocean surfaces. Characterization of oceanic whitecaps and subsurface bubbles via lidar can lead to improvements of acoustic propagation modeling. The aspects described herein can thus provides data that can be used as inputs of ocean and acoustic models to improve those models.

Figure 17:
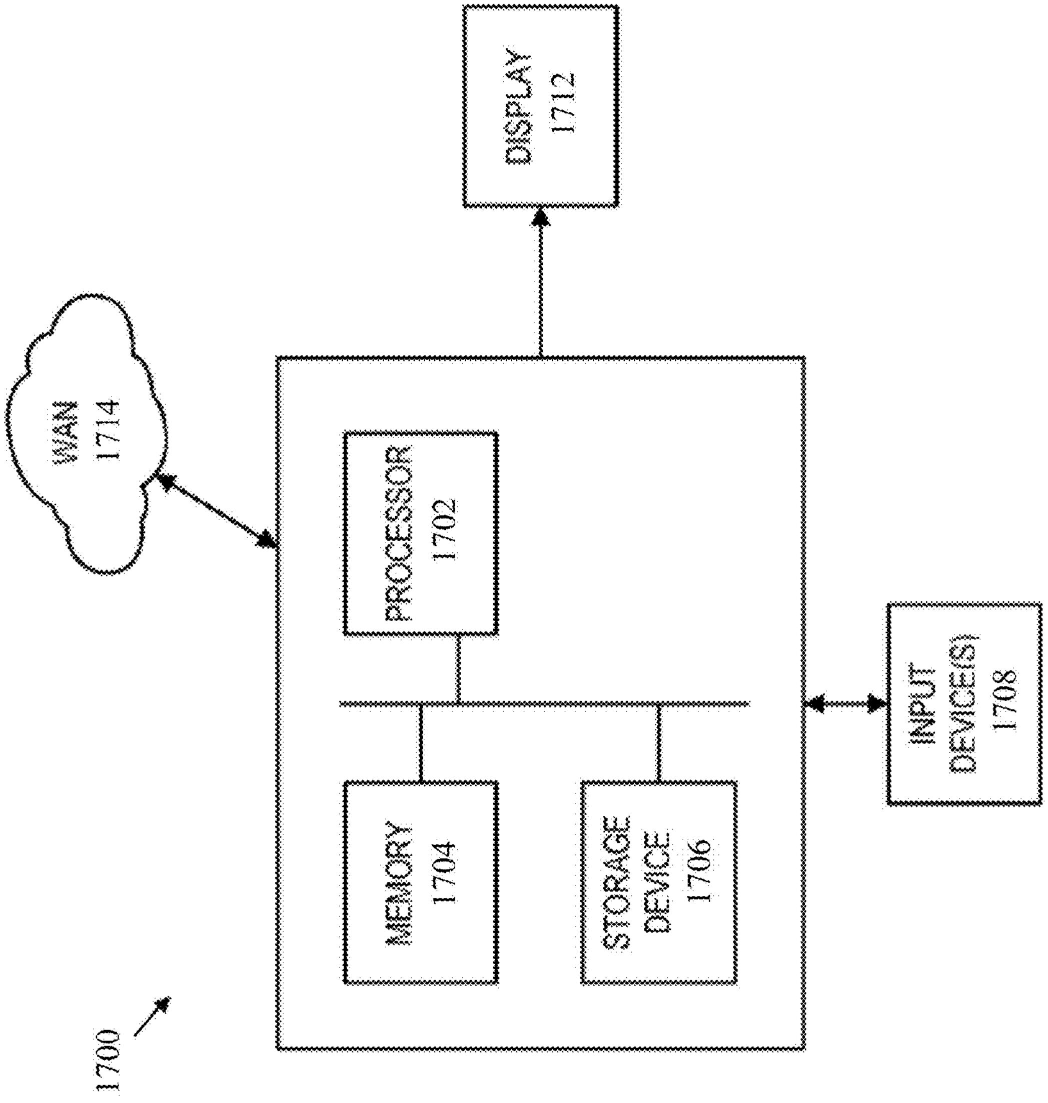
FIG. 17 illustrates an example computer system, in accordance with one or more disclosed aspects.

One or more aspects described herein may be implemented on virtually any type of computer regardless of the platform being used. For example, as shown in FIG. 17, a computer system 1700 includes a processor 1702, associated memory 1704, a storage device 1706, and numerous other elements and functionalities typical of today's computers (not shown). The computer 1700 may also include input means 1708, such as a keyboard and a mouse, and output means 1712, such as a monitor or LED. The computer system 1700 may be connected to a local may be a network (LAN) or a wide area network (e.g., the Internet) 1714 via a network interface connection (not shown). Those skilled in the art will appreciate that these input and output means may take other forms.

Further, those skilled in the art will appreciate that one or more elements of the aforementioned computer system 1700 may be located at a remote location and connected to the other elements over a network. Further, the disclosure may be implemented on a distributed system having a plurality of nodes, where each portion of the disclosure (e.g., real-time instrumentation component, response vehicle(s), data sources, etc.) may be located on a different node within the distributed system. In one embodiment of the disclosure, the node corresponds to a computer system. Alternatively, the node may correspond to a processor with associated physical memory. The node may alternatively correspond to a processor with shared memory and/or resources. Further, software instructions to perform embodiments of the disclosure may be stored on a computer-readable medium (i.e., a non-transitory computer-readable medium) such as a compact disc (CD), a diskette, a tape, a file, or any other computer readable storage device. The present disclosure provides for a non-transitory computer readable medium comprising computer code, the computer code, when executed by a processor, causes the processor to perform aspects disclosed herein.

Embodiments for detecting and/or deriving properties (e.g., characteristics) of underwater bubble clouds via lidar (e.g., shipboard lidar or the like) have been described. Although particular embodiments, aspects, and features have been described and illustrated, one skilled in the art may readily appreciate that the aspects described herein are not limited to only those embodiments, aspects, and features but also contemplates any and all modifications and alternative embodiments that are within the spirit and scope of the underlying aspects described and claimed herein. The present application contemplates any and all modifications within the spirit and scope of the underlying aspects described and claimed herein, and all such modifications and alternative embodiments are deemed to be within the scope and spirit of the present disclosure.

All references cited herein are hereby incorporated by reference into the present disclosure in their entirety.

REFERENCES

J. H. Churnside, Lidar signature from bubbles in the sea/Vol. 18, No. 8/OPTICS EXPRESS, 2010.

James H. Churnside, "Review of profiling oceanographic lidar," Opt. Eng. 53(5) 051405 (6 Dec. 2013) https://doi.org/10.1117/1.OE.53.5.051405.

H. Czerski, "Behold the bubbly ocean," Phys. World 30, 34-38 (2017).

George E. Davis, "Scattering of Light by an Air Bubble in Water," J. Opt. Soc. Am. 45, 572-581 (1955).

Dawson, K. W., Meskhidze, N., Josset, D., and Gassó, S.: Spaceborne observations of the lidar ratio of marine aerosols, Atmos. Chem. Phys., 15, 3241-3255, https://doi.org/10.5194/acp-15-3241-2015, 2015.

Derakhti, M., & Kirby, J. (2014). Bubble entrainment and liquid-bubble interaction under unsteady breaking waves. Journal of Fluid Mechanics, 761, 464-506. doi:10.1017/jfm.2014.637.

Edwin W. Eloranta, "Practical model for the calculation of multiply scattered lidar returns," Appl. Opt. 37, 2464-2472 (1998)

J. P. Fabre, G. Norton, R. Zingarelli and R. Keiffer, "An evaluation of methods for characterizing the air/water interface for parabolic equation transmission loss modeling," OCEANS 2009, 2009, pp. 1-8, doi: 10.23919/OCEANS.2009.5422257.

C. Flamant, J. Pelon, D. Hauser, C. Quentin, W. M. Drennan, F. Gohin, Chapron B., and J. Gourrion. Analysis of surface wind speed and roughness length evolution with fetch using a combination of airborne lidar and radar measurements. J. Geophys. Res., 108, 2003.

R. W. Gould, Jr., D. Josset, S. Anderson, W. Goode, R. N. Conmy, B. Schaeffer, S. Pearce, T. Mudge, J. Bartlett, D. Lemon, D. Billenness, O. Garcia (2019); Estimating Oil Slick Thickness with LiDAR Remote Sensing Technology; Bureau of Safety and Environmental Enforcement (BSEE) Oil Spill Response Research Branch; https://www.bsee.gov/sites/bsee.gov/files/research-reports//1091aa.pdf.

Y. Hu, Z. Liu, D. Winker, M. Vaughan, V. Noel, L. Bissonnette, G. Roy, and Matthew McGill; Simple relation between lidar multiple scattering and depolarization for water clouds. Opt. Lett., 31 (12):1809-1811, 2006.

Hu, Y., Stamnes, K., Vaughan, M., Pelon, J., Weimer, C., Wu, D., Cisewski, M., Sun, W., Yang, P., Lin, B., Omar, A., Flittner, D., Hostetler, C., Trepte, C., Winker, D., Gibson, G., and Santa-Maria, M.: Sea surface wind speed estimation from space-based lidar measurements, Atmos. Chem. Phys., 8, 3593-3601, https://doi.org/10.5194/acp-8-3593-2008, 2008.

Hogan, R. J. (2008). Fast Lidar and Radar Multiple-Scattering Models. Part I: Small-Angle Scattering Using the Photon Variance-Covariance Method, Journal of the Atmospheric Sciences, 65(12), 3621-3635. Retrieved Nov. 18, 2021, from https://journals.ametsoc.org/view/journals/atsc/65/12/2008jas2642.1.xml.

C. A. Hostetler, Z. Liu, J. Reagan, M. Vaughan, D. Winker, M. Osborn, W. H. Hunt, K. A. Powell, and C. Trepte. CALIOP Algorithm Theoretical Basis Document: Calibration and level 1 data products, 2006.

Josset, D., P. Zhai, Y. Hu, J. Pelon, and P. L. Lucker, Lidar equation for ocean surface and subsurface, Opt. Express 18, 20862-20875, (2010b).

Josset, D., J. Pelon, and Y. Hu, Multi-instrument calibration method based on a multiwavelength ocean surface model, IEEE Geoscience and Remote Sensing letter, 7, 195-199, doi:10.1109/LGRS.2009.2030906, (2010a).

Kar, J., Vaughan, M. A., Lee, K. P., Tackett, J. L., Avery, M. A., Garnier, A., Getzewich, B. J., Hunt, W. H., Josset, D., Liu, Z., Lucker, P. L., Magill, B., Omar, A. H., Pelon, J., Rogers, R. R., Toth, T. D., Trepte, C. R., Vernier, J. P., Winker, D. M., and Young, S. A.: CALIPSO lidar calibration at 532 nm: version 4 nighttime algorithm, Atmos. Meas. Tech., 11, 1459-1479, https://doi.org/10.5194/amt-11-1459-2018, 2018.

Alexander A Kokhanovsky 2002 J. Opt. A: Pure Appl. Opt. 5 47.

Zhujun Li, David Painemal, Gregory Schuster, Marian Clayton, Richard Ferrare, Damien Josset, Jayanta Kar, and Charles Trepte, Assessment of tropospheric CALIPSO Version 4.2 aerosol types over the ocean using independent CALIPSO-SODA lidar ratios, amt-2021-378.

R. T. Menzies, D. M. Tratt, and W. H. Hunt. Lite measurements of sea surface directional reflectance and the link to surface wind speed. Appl. Opt., 37:5550-5559, 1998.

Morel, A., Maritorena, S., 2001. Bio-optical properties of oceanic waters: A reappraisal.

J. Geophys. Res. Oceans 106 (C4), 7163-7180.

Walter Munk, An Inconvenient Sea Truth: Spread, Steepness, and Skewness of Surface Slopes, Annual Review of Marine Science 2009 1:1, 377-415.

J. C. Novarini, R. S. Keiffer, and G. V. Norton, "A model for variations in the range and depth dependence of the sound speed and attenuation induced by bubble clouds under wind-driven sea surfaces," IEEE J. oceanic Eng., 23, 423-438, 1998.

Lord Rayleigh. On the light from the sky, its polarization and colour. Phil. Mag., XLI:107-120, 1871.

Remer, L. A., et al. (2008), Global aerosol climatology from the MODIS satellite sensors, J. Geophys. Res., 113, D14S07, doi:10.1029/2007JD009661.

Seitz, R. Bright water: hydrosols, water conservation and climate change. Climatic Change 105, 365-381 (2011). https://doi.org/10.1007/s10584-010-9965-8. Markus Selmke, "Bubble optics," Appl. Opt. 59, 45-58 (2020).

Thomson, J. (2012). Wave Breaking Dissipation Observed with "SWIFT" Drifters, Journal of Atmospheric and Oceanic Technology, 29(12), 1866-1882. Retrieved Nov. 18, 2021, from https://journals.ametsoc.org/view/journals/atot/29/12/jtech-d-12-00018_1.xml J. Thomson et al., "A new version of the SWIFT platform for waves, currents, and turbulence in the ocean surface layer," 2019 IEEE/OES Twelfth Current, Waves and Turbulence Measurement (CWTM), 2019, pp. 1-7, doi: 10.1109/CWTM43797.2019.8955299.

S. Vagle and D. M. Farmer, "The measurement of bubble-size distribution by acoustical backscatter," J. Atmos. and Ocean. Tech., 8 630-644, 1991.

D. Wang, D. Josset, I. Savelyev, M. Anguelova, S. Cayula, and A. Abelev, An experimental study on measuring breaking-wave bubbles with LiDAR remote sensing, MDPI Remote Sensing.

Woolf, D. K., I. Leifer, P. Nightingale, T S. Rhee, P. Bowyer, G. Caulliez, G. de Leeuw, S. Larsen, M. Liddicoat, J. Baker, and M. O. Andreae. 2007. Modelling of bubble-mediated gas transfer; Fundamental principles and a laboratory test, Journal of Marine Systems, 66(1-4), 71-91.

M. Xu and R. R. Alfano. Random walk of polarized light in turbid media. Phys. Rev. Lett., 95:213901-1-4, 2005.

A. T. Young. Rayleigh scattering. Phys. Today, pages 42-48, 1982.

What is claimed is:

1. A method comprising:

receiving, by a computing device, lidar data, the lidar data being associated with remote sensing of moving water;

calibrating, by the computing device, the lidar data, the calibration being based on one or more measurements contemporaneously measured with remote sensing of the moving water;

refining, by the computing device, the calibrated lidar data, the refinement being based on bubble detection associated with the moving water, wherein the refining comprises discriminating between one or more signals associated with the bubble detection and one or more signals associated with non-bubble background detection;

determining, from the refined lidar data and by the computing device, a bubble mask via feature detection based on depolarization ratio; and determining, based on the bubble mask and by the computing device, one or more bubble characteristics associated with the moving water.

2. The method of claim 1, wherein the one or more bubble characteristics comprise void fraction of a bubble cloud associated with the moving water, injection rate of bubbles associated with the moving water, or decay rate of diffused bubbles associated with the moving water.

3. The method of claim 1, wherein determining the one or more bubble characteristics is based on a threshold associated with a depolarization defined by a ratio of a cross-polarization channel on a co-polarization channel.

4. The method of claim 3, further comprising identifying bubbles as having a depolarization ratio larger than 0.015.

5. The method of claim 1, wherein depolarization associated with the lidar data varies based on bubble size distribution.

6. The method of claim 1, wherein the remote sensing of moving water is performed over a predetermined sampling window of time.

7. The method of claim 6, wherein the window of time is about 30 minutes.

8. The method of claim 1, where determining the one or more bubble characteristics comprises determining a backscatter coefficient associated with the moving water, wherein a value of the backscatter coefficient is related to the one or more bubble characteristics.

9. The method of claim 8, where determining the one or more bubble characteristics further comprises determining a void fraction associated with the moving water based on the determined backscatter coefficient.

10. The method of claim 8, wherein the backscatter coefficient is based on a backscatter direction angle varying based on a distance above a surface of the moving water at which the lidar data is captured.

11. The method of claim 10, wherein the backscatter direction angle varies based on a boat attitude or wave height change.

12. The method of claim 8, wherein determining the backscatter coefficient further comprises determining a correction to the one or more signals associated with the bubble detection based on contribution of water molecule scattering and attenuation of water molecules.

13. The method of claim 12, wherein the scattering is determined from a measurement of air temperature or pressure.

14. The method of claim 12, wherein a backscatter intensity located immediately below bubble clouds is used to determine an attenuation of scattering by water molecules.

15. The method of claim 12, wherein the calibration is performed with the average of the lidar data between captured at about 3.5 and 4.2 meters above a surface of the moving water.

16. The method of claim 1, wherein the calibrating comprises removing an influence of a signal associated with a sea spray event, wherein the calibration is based on an atmospheric backscatter coefficient value equal to about a median value associated with the received lidar data.

17. The method of claim 1, where the one or more bubble characteristics comprises a bubble depth being associated with a number of continuous data points identified as bubble signals below a water surface associated with the moving water.

18. The method of claim 1, further comprising determining, based on the bubble mask, a maximum penetration depth associated with the one or more bubble characteristics.

19. The method of claim 1, further comprising categorizing the one or more bubble characteristics into one of the following categories: bubbleless ocean associated with low surface and subsurface depolarization, whitecaps associated with high surface depolarization with low subsurface depolarization, extended bubble clouds associated with large surface and subsurface depolarization, or underwater bubble clouds associated with low surface and large subsurface depolarization.

20. The method of claim 1, wherein the one or more bubble characteristics comprises a decay rate of diffused bubbles.

21. The method of claim 1, wherein the moving water is comprised in a large-scale body of water.

22. The method of claim 1, wherein the lidar data is captured by a lidar device attached to a water-based vessel.

23. The method of claim 1, wherein the calibrating is based on atmospheric scattering.

* * * * *